US 11,376,428 B2

(12) United States Patent
Irazoqui et al.

(10) Patent No.: US 11,376,428 B2
(45) Date of Patent: Jul. 5, 2022

(54) PREVENTION OF REFLUX INDUCED LARYNGOSPASM

(71) Applicant: Purdue Research Foundation, West Lafayette, IN (US)

(72) Inventors: Pedro Irazoqui, Lafayette, IN (US); Ryan Benjamin Budde, Indianapolis, IN (US); Daniel Pederson, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 29 days.

(21) Appl. No.: 16/403,191

(22) Filed: May 3, 2019

(65) Prior Publication Data

US 2019/0336758 A1 Nov. 7, 2019

Related U.S. Application Data

(60) Provisional application No. 62/667,328, filed on May 4, 2018.

(51) Int. Cl.
| | |
|---|---|
| *A61N 1/36* | (2006.01) |
| *A61B 5/00* | (2006.01) |
| *A61N 1/05* | (2006.01) |
| *A61B 5/113* | (2006.01) |
| *A61B 5/145* | (2006.01) |
| *A61B 5/0205* | (2006.01) |

(52) U.S. Cl.
CPC ............ *A61N 1/3601* (2013.01); *A61B 5/113* (2013.01); *A61B 5/14539* (2013.01); *A61B 5/4809* (2013.01); *A61N 1/0517* (2013.01); *A61B 5/0205* (2013.01); *A61B 2503/04* (2013.01); *A61B 2562/0219* (2013.01); *A61N 1/36064* (2013.01)

(58) Field of Classification Search
CPC ................ A61N 1/3601; A61N 1/0517; A61N 1/36064; A61B 5/113; A61B 5/0205; A61B 2562/0219
See application file for complete search history.

(56) References Cited

U.S. PATENT DOCUMENTS

| | | | | |
|---|---|---|---|---|
| 9,202,008 | B1* | 12/2015 | Frederick | A61B 5/7282 |
| 9,681,836 | B2* | 6/2017 | Sabesan | A61B 5/7253 |
| 2009/0014012 | A1* | 1/2009 | Sanders | A61N 1/0548 |
| | | | | 128/848 |
| 2010/0280337 | A1* | 11/2010 | Peters | A61B 5/053 |
| | | | | 600/301 |
| 2013/0197321 | A1* | 8/2013 | Wilson | A61N 1/3601 |
| | | | | 600/301 |

(Continued)

OTHER PUBLICATIONS

Nakase, K., et. al; Laryngospasm, central and obstructive apnea during seizures: Defining pathophysiology for sudden death in a rat model; Dec. 2016; Epilepsy Research; vol. 128; pp. 126-139 (Year: 2016).*

(Continued)

*Primary Examiner* — Nathan J Jenness
*Assistant Examiner* — Skylar Lindsey Christianson
(74) *Attorney, Agent, or Firm* — Fish & Richardson P.C.

(57) ABSTRACT

Systems and techniques can prevent reflux induced laryngospasm and the pathologies resulting therefrom, including (but not limited to) sudden death in epilepsy (SUDEP) and sudden infant death syndrome (SIDS).

18 Claims, 10 Drawing Sheets

(56) References Cited

U.S. PATENT DOCUMENTS

| | | | | |
|---|---|---|---|---|
| 2015/0282755 | A1* | 10/2015 | Deriche | A61B 5/374 600/301 |
| 2016/0045741 | A1* | 2/2016 | Libbus | A61N 1/36057 607/44 |
| 2016/0106366 | A1* | 4/2016 | Banet | A61B 5/6822 600/301 |
| 2017/0143280 | A1* | 5/2017 | Kent | A61F 5/566 |

OTHER PUBLICATIONS

Aiba, et al., "Spreading depolarization in the brainstem mediates sudden cardiorespiratory arrest in mouse SUDEP models," Science Translational Medicine, 2015, 7(282):282ra46, 10 pages.

Athanasakis, et al., "The factors contributing to the risk of sudden infant death syndrome," Hippokratia, 2011, 15:127-131.

Barnard, "A New Test for 2×2 Tables," Nature, 1945, 156:177.

Bateman, et al., "Ictal hypoventilation contributes to cardiac arrhythmia and SUDEP: Report on two deaths in video-EEG-monitored patients," Epilepsia, 2010, 51:916-920.

Berg, "Mortality in epilepsy," Epilepsy Currents, 2001, 1:28-30.

Bird, et al., "Sudden unexplained death in epilepsy: an intracranially monitored case," Epilepsia, 1997, 38:S52-S56.

Brodie, "Road to refractory epilepsy: the Glasgow story," Epilepsia, 2013, 54:5-8.

Buchhalter, et al., "Partners Against Mortality in Epilepsy Conference Summary," Epilepsy Currents, 2013, 13(2):5-21.

Budde et al, "Acid reflux induced laryngospasm as a potential mechanism of sudden death in epilepsy," Epilepsy Research, 2018, pp. 23-31.

Budde et al, "Mechanisms and prevention of acid reflux induced laryngospasm in seizing rats," Purdue University, 2019, 46 pages.

Caflisch, et al., "Manufacture and utilization of antimony pH electrodes," Kidney International, 1978, 14:126-141.

Crosby, et al., "Modulation of activity and conduction in single dorsal column axons by kilohertz-frequency spinal cord stimulation," Journal of Neurophysiology, 2017, 117:136-147.

Davies, et al., "Upper airway chemoreflex responses to saline and water in preterm infants," Journal of Applied Physiology, 1988, 64:1412-1420.

Debas and Carvajal, "Vagal regulation of acid secretion and gastrin release," Yale J. Biol. Med., 1994, 67:145-151.

Devinsky, "Sudden, unexpected death in epilepsy," N. Engl. J. Med., 2011, 365:1801-1811.

Devinsky, et al., "Sudden unexpected death in epilepsy: epidemiology, mechanisms, and prevention," Lancet Neurol., 2016, 15:1075-1088.

Donnelly, et al., "Serotonin in the solitary tract nucleus shortens the laryngeal chemoreflex in anaesthetized neonatal rats," Exp. Physiol., 2016, 101:946-961.

Dravet and Oguni, "Dravet syndrome (severe myoclonic epilepsy in infancy)," Handbook of Clinical Neurology, Dulac, Lassonde, Sarnat, (Eds.), 2013, Chapter 65, 627-633.

Finnerty and Jefferys, "9-16 Hz Oscillation precedes secondary generalization of seizures in the rat tetanus toxin model of epilepsy," Journal of Neurophysiology, 2000, 83:2217-2226.

Genton, et al., "Dravet syndrome: The long-term outcome," Epilepsia, 2011, 52(Suppl. 2):44-49.

Goding, "Correlation of laryngeal chemoreflex severity with laryngeal muscle response," 1998, 108:863-872.

Halstead, "Role of gastroesophageal reflux in pediatric upper airway disorders," Otolaryngol. Head Neck Surg., 1999, 120:208-214.

Hassel, et al., "An agar-based silver|silver chloride reference electrode for use in micro-electrochemistry," Electrochem. Commun., 1999, 1:180-183.

He, et al., "Symptomatic diffuse esophageal spasm as a major ictal manifestation of post-traumatic epilepsy: a case report," Dis. Esophagus, 2013, 26:327-330.

Heman-Ackah, et al., "The laryngeal chemoreflex: An evaluation of the normoxic response," Laryngoscope, 2009, 119:370-379.

Horn, et al., "Why can't rodents vomit? A comparative behavioral, anatomical, and physiological study," PLoS One, 2013, 8:e60537, 16 pages.

Itoh, et al., "The negative feedback mechanism of gastric acid secretion: Significance of acid in the gastric juice in man and dog," Surgery, 1975, 77:648-660.

Jensen, et al., "Fasting of mice: a review," Laboratory Animals, 2013, 47:225-240.

Johnson, "Effects of somatostatin and acid on inhibition of gastrin release in newborn rats," Endocrinology, 1984, 114:743-746.

Kilgore and Bhadra, "Reversible nerve conduction block using kilohertz frequency alternating current," Neuromodulation, 2014, 17:242-255.

Kinney and Thach, "The sudden infant death syndrome," N. Engl. J. Med., 2009, 361:795-805.

Lacuey et al., "Ictal laryngospasm monitored by video-EEG and polygraphy: a potential SUDEP mechanism," Epileptic Disord., 2018, 20(2):146-150.

Lamberts, et al., "Sudden unexpected death in epilepsy: People with nocturnal seizures may be at highest risk," Epilepsia, 2011, 53:253-257.

Langan, et al., "Sudden unexpected death in epilepsy: a series of witnessed deaths," J. Neurol. Neurosurg. Psychiatry, 2000, 68:211-213.

Lhatoo, et al., "Nonseizure SUDEP: sudden unexpected death in epilepsy without preceding epileptic seizures," Epilepsia, 2016, 57:1161-1168.

Loughlin, et al., "Acid-induced laryngospasm in a canine model," Laryngoscope, 1996, 106:1506-1509.

Lutsi and Hirano, "Ambulatory pH monitoring: new advances and indications," Gastroenterol. Hepatol., 2006, 2:835-842.

Marchal, et al., "Reflex apnea from laryngeal chemo-stimulation in the sleeping premature newborn lamb," Pediatric Research, 1982, 16:621-627.

Marks, et al., "Measurement of respiratory rate and timing using a nasal thermocouple," Journal of Clinical Monitoring, 1995, 11:159-164.

Massey, et al., "Mechanisms of sudden unexpected death in epilepsy: the pathway to prevention," Nat. Rev. Neurol., 2014, 10:271-282.

McGraw, "Swimming behavior of the human infant," Journal of Pediatrics, 1939, 15:485-490.

McLean and Wimalaratna, "Sudden death in epilepsy recorded in ambulatory EEG," J. Neurol. Neurosurg. Psychiatry, 2007, 78:1395-1397.

Mirza, et al., "Influence of Cholecystokinin-8 on compound nerve action potentials from ventral gastric vagus in rats," International Journal of Neural Systems, 2018, 28:1850006, 17 pages.

Mor, et al., "Quantitative video laryngoscopy to monitor recovery from recurrent laryngeal nerve injury in the rat," Otolaryngol. Head Neck Surg., 2014, 150:824-826.

Murphy, et al., "Deaths: Final Data for 2010," NIH, National Vital Statistics Reports, 2013, 61(4), 118 pages.

Naggar and Stewart, "A rat model for exploring the contributions of ventricular arrhythmias to sudden death in epilepsy," Sudden Unexpected Death in Epilepsy: Mechanisms and New Methods for Analyzing Risks, 2015, Chapter 25, 241-250.

Nakase, et al., "Laryngospasm, central and obstructive apnea during seizures: Defining pathophysiology for sudden death in a rat model," Epilepsy Research, 2016, 128:126-139.

Nashef, et al., "Unifying the definitions of sudden unexpected death in epilepsy," Epilepsia, 2012, 53:227-233.

Nobili, et al., "Sudden unexpected death in epilepsy (SUDEP) and sleep," Sleep Medicine Reviews, 2011, 15:237-246.

Orenstein, "An overview of reflux-associated disorders in infants: apnea, laryngospasm, and aspiration," The American Journal of Medicine, 2001, 111:60-63.

Pederson, et al., "The bionode: A closed-loop neuromodulation implant," ACM Transactions on Embedded Computing Systems, 2019, 18(1):9, 20 pages.

(56) References Cited

OTHER PUBLICATIONS

Postma and Halum, "Laryngeal and pharyngeal complications of gastroesophageal reflux disease," GI Motil. Online, 2006, retrieved on Oct. 3, 2019, retrieved from URL <https://www.nature.com/gimo/contents/pt1/full/gimo46.html>, 19 pages.

Qing, et al., "B fibers are the best predictors of cardiac activity during Vagus nerve stimulation," Bioelectronic Medicine, 2018, 4:5, 11 pages.

Ryvlin, et al., "Incidence and mechanisms of cardiorespiratory arrests in epilepsy monitoring units (MORTEMUS): a retrospective study," Lancet Neurol., 2013, 12:966-977.

Saito, et al., "Repeatable focal seizure suppression: A rat preparation to study consequences of seizure activity based on urethane anesthesia and reversible carotid artery occlusion," Journal of Neuroscience Methods, 2006, 155:241-250.

Sakamoto, et al., "Autonomic consequences of kainic acid—induced limbic cortical seizures in rats: Peripheral autonomic nerve activity, acute cardiovascular changes, and death," Epilepsia, 2008, 49:982-996.

Scadding et al., "Laryngeal inflammation in the sudden infant death syndrome," Current Pediatric Reviews, 2014, 10:309-313.

Schirmer, "Current status of proximal gastric vagotomy," Ann. Surg., 1989, 209:131-148.

Selassie, 2015. Risk Factors of Epilepsy Outcomes: Comorbidities in Population with Epilepsy in South Carolina.

Sowers, et al., "Sudden unexpected death in epilepsy: Fatal postictal respiratory and arousal mechanisms," Respir. Physiol. Neurobiol., 2013, 189:315-323.

Stewart, et al., "Obstructive apnea due to laryngospasm links ictal to postictal events in SUDEP cases and offers practical biomarkers for review of past cases and prevention of new ones," Epilepsia, 2017, 58:e87-e90.

Tao, et al., "SUDEP, suspected positional airway obstruction, and hypoventilation in postictal coma," Epilepsia, 2010, 51:2344-2347.

Tavee and Morris, "Severe postictal laryngospasm as a potential mechanism for sudden unexpected death in epilepsy: a near-miss in an EMU," Epilepsia, 2008, 49:2113-2117.

Thurman, et al., "Sudden unexpected death in epilepsy: Assessing the public health burden," Epilepsia, 2014, 55:1479-1485.

Van Der Velde, et al., "Prolongation of the laryngeal chemoreflex after inhibition of the rostral ventral medulla in piglets: a role in SIDS?" Journal of Applied Physiology, 2003, 94:1883-1895.

Vela, et al., Laryngopharyngeal Reflux, Practical Manual of Gastroesophageal Reflux Disease, 1st ed. John Wiley & Sons, Ltd., 2013, Chapter 10, 154-160.

Ward, et al., "A flexible platform for biofeedback-driven control and personalization of electrical nerve stimulation therapy," IEEE Transactions on Neural Systems and Rehabilitation Engineering, 2015, 23:475-484.

WebMD [online], "Acetazolamide side effects," available no later than 2018, retrieved from URL <https://www.webmd.com/drugs/2/drug-6755/acetazolamide-oral/details>, 2 pages.

WebMD, [online], "Carbamazepine side effects," available no later than 2018, retrieved from URL <https://www.webmd.com/drugs/2/drug-1493-5/carbamazepine-oral/carbamazepine-oral/details>, 2 pages.

WebMD, [online], "Clobazam side effects," available no later than 2018, retrieved from URL <https://www.webmd.com/drugs/2/drug-158673-1981/clobazam-oral/clobazam-film-oral/details>, 2 pages.

WebMD, [online], "Ethosuximide side effects," available no later than 2018, retrieved from URL <https://www.webmd.com/drugs/2/drug-7099/ethosuximide-oral/details>, 2 pages.

WebMD [online], "Gabapentin side effects," available no later than 2018, retrieved from URL <https://www.webmd.com/drugs/2/drug-14208-8217/gabapentin-oral/gabapentin-oral/details>, 2 pages.

WebMD [online], "Levetiracetam side effects," available no later than 2018, retrieved from URL <https://www.webmd.com/drugs/2/drug-17855-1750/levetiracetam-oral/levetiracetam-tablet-for-oral-suspension/details>, 2 pages.

White, Jr., et al., "Excitation of neurons in the medullary raphe increases gastric acid and pepsin production in cats," Am J Physiol.-Gastrointestinal and Liver Physiology, 1991, 260(1):G91-G96.

Xia, et al., "Laryngeal reflex apnea in neonates: Effects of CO2 and the complex influence of hypoxia," Respir. Physiol. Neurobiol., 2013, 186:109-113.

Yang, et al., "Activation of the parapyramidal region in the ventral medulla stimulates gastric acid secretion through vagal pathways in rats," Neurosci., 2000, 95:773-779.

Zack and Kobau, "National and state estimates of the numbers of adults and children with active epilepsy—United States, 2015," MMWR Morb. Mortal. Wkly. Rep., 2017, 66(31):821-825.

\* cited by examiner

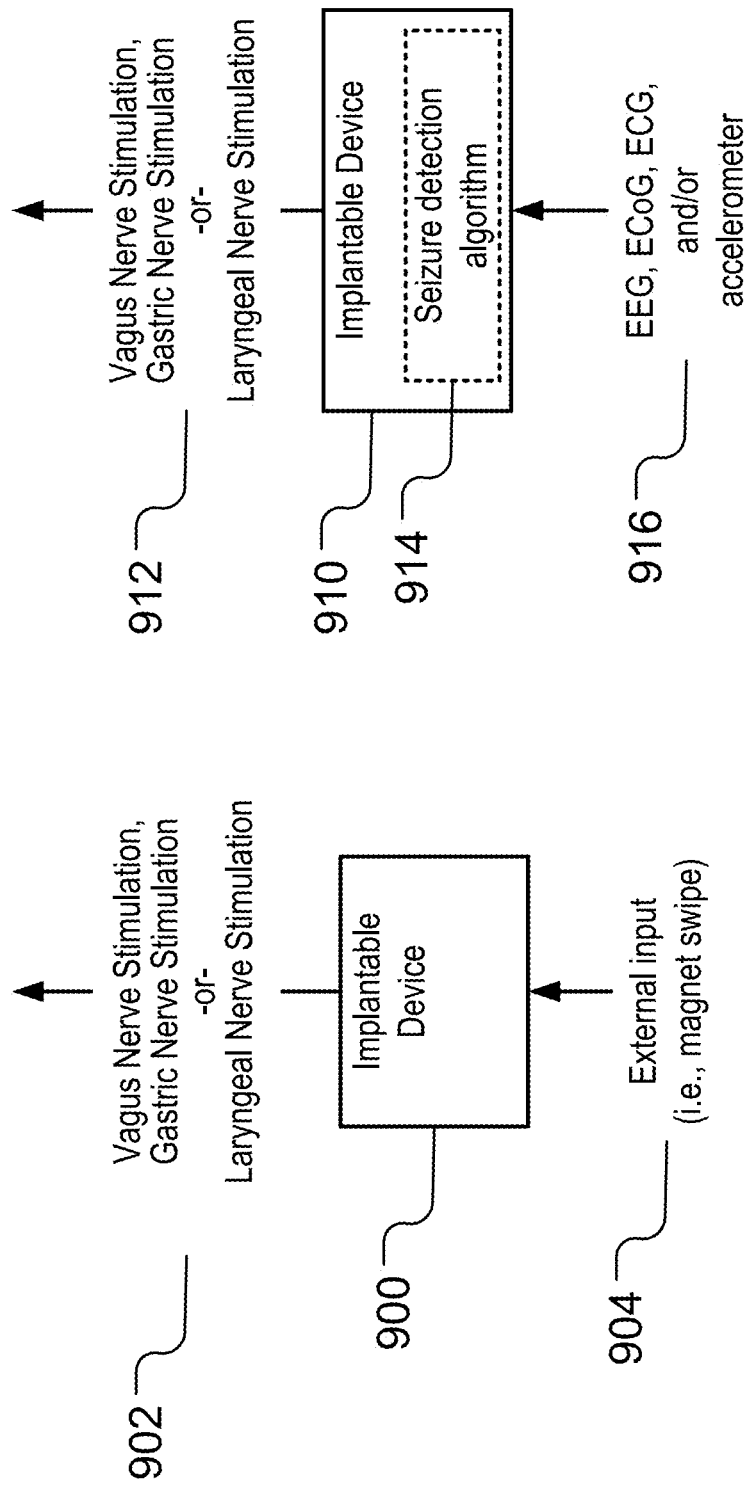

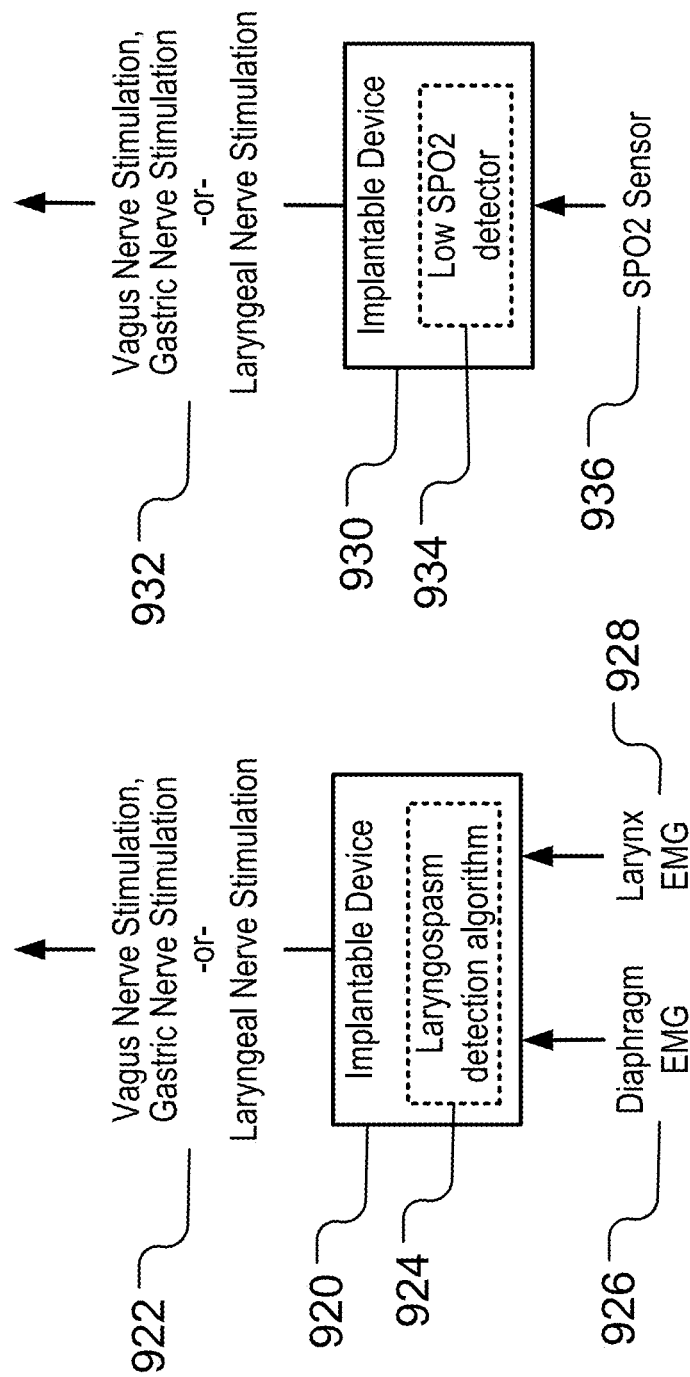

PREVENTION OF REFLUX INDUCED LARYNGOSPASM

CROSS-REFERENCE TO RELATED APPLICATIONS

This application claims the benefit of U.S. Provisional Application Ser. No. 62/667,328, filed May 4, 2018. The disclosure of the prior application is considered part of (and is incorporated by reference in) the disclosure of this application. This application also incorporates by reference International Patent Application number PCT/US2017/037079.

STATEMENT OF FEDERALLY SPONSORED RESEARCH

This invention was made with government support under OD 023847 awarded by the National Institutes of Health. The government has certain rights in the invention.

BACKGROUND

1. Technical Field

This document relates to reflux and, more particularly, the prevention of reflux induced laryngospasm and any associated pathology resulting therefrom, including (but not limited to) sudden death in epilepsy (SUPED) and sudden infant death syndrome (SIDS).

2. Background Information

Sudden unexpected death in epilepsy (SUDEP) is a complication of epilepsy which is defined as a "sudden, unexpected, witness or unwitnessed, nontraumatic and nondrowning death in patients with epilepsy, with or without evidence for a seizure and excluding documented status epilepticus, in which postmortem examination does not reveal a toxicologic or anatomic cause of death."

There is growing evidence that laryngospasm may be linked to sudden unexpected death in epilepsy (SUDEP). There are an estimated 3.4 million Americans—including 470,000 children—living with epilepsy. In approximately 30% of cases seizures cannot be controlled by medication, and uncontrolled seizures are the primary risk factor for SUDEP. In the US, the annual mortality rate for SUDEP in patients with epilepsy is approximately 1.2/1000, which translates to as many as 4,000 unexpected deaths per year within an at-risk population in excess of 1 million.

SUMMARY

This document describes methods and materials for the prevention of reflux induced laryngospasm and any associated pathology resulting therefrom, including (but not limited to) sudden death in epilepsy (SUPED) and sudden infant death syndrome (SIDS).

In one aspect, this disclosure is directed to a method of preventing sudden death. The method includes detecting at least one of a reflux or a laryngospasm and transmitting an alert to a device in response to detecting at least one of the reflux or the laryngospasm.

In some cases, detecting at least one of the reflux or the laryngospasm can include detecting rising acid in an esophagus via a pH sensor. In some cases, detecting at least one of the reflux or the laryngospasm can include detecting a change in electrical activity of a diaphragm or a larynx via an EMG. In some cases, detecting at least one of the reflux or the laryngospasm can include detecting a change in $SpO_2$. In some cases, the method can further include providing electrical stimulation to a nerve, where the electrical stimulation is configured to cause the at least one of the reflux or the laryngospasm to cease. In some cases, the nerve can be a vagus nerve or a gastric nerve. In some cases, the electrical stimulation can be provided by an implanted device. In some cases, the electrical stimulation can be triggered by an external input. In some cases, the external input can be a magnet swipe. In some cases, the electrical stimulation can be provided by an external device. In some cases, the electrical stimulation can be configured to prevent at least one of sudden unexplained death from epilepsy (SUDEP) or sudden infant death syndrome (SIDS).

In another aspect, this disclosure is directed to a method of preventing sudden infant death syndrome (SIDS). The method includes detecting movement of the infant while sleeping via an accelerometer and transmitting an alert to a device in response to detecting movement. In some cases, the accelerometer can be located on the infant. In some cases, the accelerometer can be located on a bed.

In yet another aspect, this disclosure is directed to a method of preventing sudden death. The method includes detecting at least one of a reflux or a laryngospasm and providing electrical stimulation to a laryngeal nerve in response to detecting at least one of the reflux or the laryngospasm.

In some cases, detecting at least one of the reflux or the laryngospasm can include detecting rising acid in an esophagus via a pH sensor. In some cases, detecting at least one of the reflux or the laryngospasm can include detecting electrical activity of a diaphragm or a larynx via an EMG. In some cases, the electrical stimulation can be configured to open the larynx. In some cases, the electrical stimulation can be provided by an implanted device. In some cases, the electrical stimulation can be triggered by an external input. In some cases, the external input can be a magnet swipe. In some cases, the electrical stimulation can be provided by an external device. In some cases, the external device can be placed on a neck of a patient.

In yet another aspect, this disclosure is directed to a method for preventing sudden unexplained death from epilepsy (SUDEP). The method includes detecting a seizure and providing electrical stimulation to electrically block a nerve, where the electrical stimulation is configured to prevent a stomach from filing with acid.

In some cases, detecting a seizure can include detecting a cessation of respiration. In some cases, detecting a cessation of respiration can include detecting a change in electrical activity of a diaphragm or a larynx via an EMG. In some cases, detecting a cessation of respiration can include detecting a cessation of movement of air in and out of a lung via a thermistor. In some cases, the nerve can be at least one of a vagus nerve or a gastric nerve.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the invention are set forth in the accompanying drawings and the description below. Other features, objects, and advantages of the invention will be apparent from the description, drawings, and from the claims.

DESCRIPTION OF DRAWINGS

FIG. 9 illustrates a first stimulation system for vagal nerve stimulation or laryngeal nerve stimulation, in accordance with some embodiments provided herein.

FIG. 10 illustrates a second stimulation system for vagal nerve stimulation or laryngeal nerve stimulation, in accordance with some embodiments provided herein.

FIG. 11 illustrates a third stimulation system for vagal nerve stimulation or laryngeal nerve stimulation, in accordance with some embodiments provided herein.

FIG. 12 illustrates a fourth stimulation system for vagal nerve stimulation or laryngeal nerve stimulation, in accordance with some embodiments provided herein.

Like reference numbers represent corresponding parts throughout.

DETAILED DESCRIPTION

This document describes methods and materials for the prevention of reflux induced laryngospasm and any associated pathology resulting therefrom, including (but not limited to) sudden death in epilepsy (SUPED) and sudden infant death syndrome (SIDS).

The exact cause of SUDEP is unknown, but respiratory and cardiac dysfunction are believed to play a crucial role. Laryngospasm has been proposed as a potential cause. The potential link between laryngospasm and sudden death in a kainic acid (KA) model of epilepsy has been explored in rats and it was observed that obstructive apnea via laryngospasm is associated with cardiac dysfunction, $SpO_2$ decline, and death, while central apnea is not. Further, in certain studies it has been observed that in every instance of obstructive apnea there was sudden death. Anecdotal clinical data supports this mechanism as one possible cause of SUDEP in humans. Sudden infant death syndrome (SIDS) kills approximately 2,000 infants every year in the US. While the risk for SIDS can be reduced by placing a baby in the supine (not prone) position during sleep, the exact causes are elusive. The present disclosure addresses these massive and tragic unmet needs.

Figure 1:
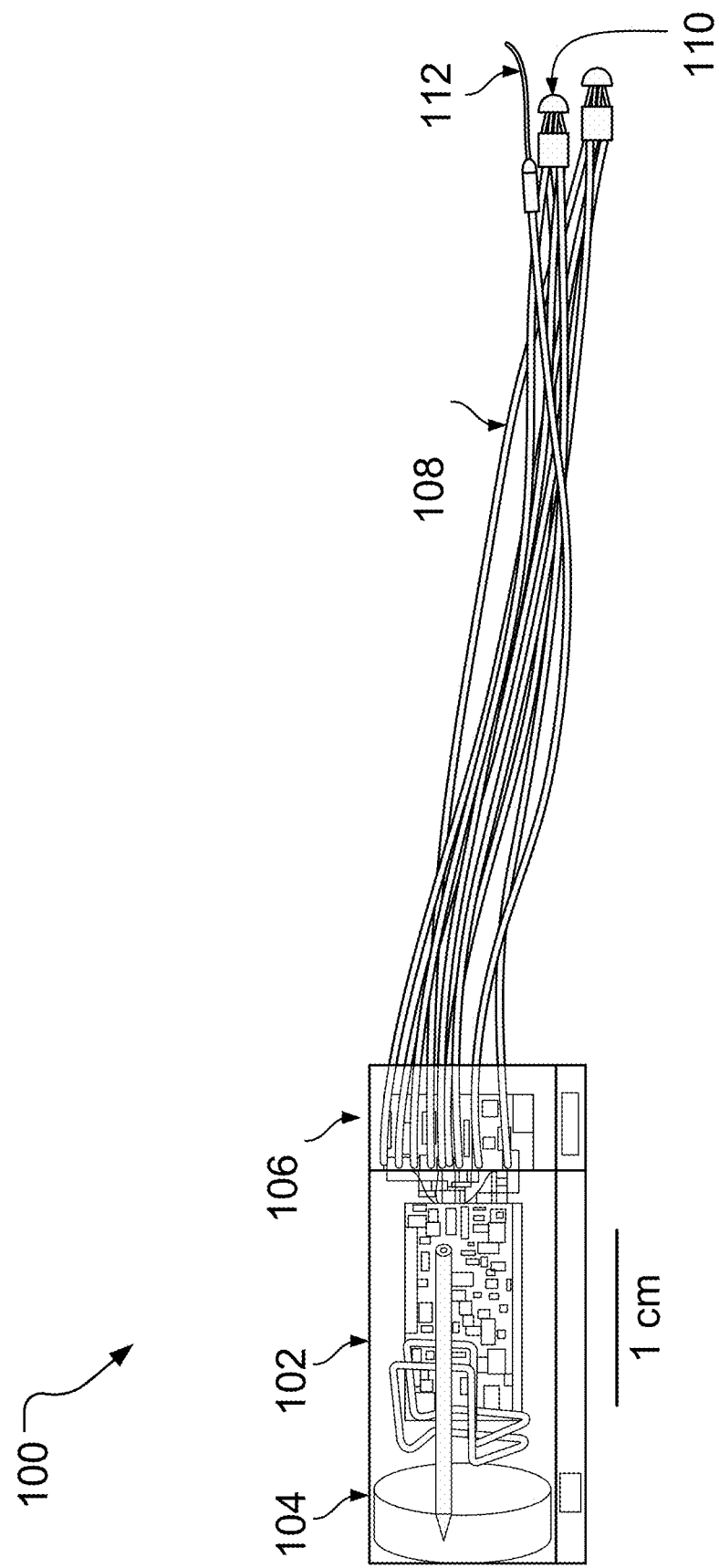
FIG. 1 is an implantable electroceutical for preventing laryngospasm, in accordance with some embodiments provided herein.

Referring to FIG. 1, an implantable electroceutical device 100 is configured to prevent fatal laryngospasm, specifically acid reflux induced laryngospasm. The implantable electroceutical device 100 can include a glass tube 102 with a seal 104 at a proximal end. A feedthrough 106 can be located at a distal end of the tube 102 such that helical lead 108 can extend distally from the tube 102. A recording tip 110 can be located at a distal end portion of one or more of the helical leads 108. Additionally, a respiratory thermocouple 112 can be located a distal end portion of another of one or more of the helical leads 108.

The implantable electroceutical device 100 is of the type disclosed in commonly-owned and co-pending International Patent Application Number PCT/US2017/037079 titled "System for Wireless Recording and Stimulating of Bioelectric Events" filed 12 Jun. 2017 and published 14 Dec. 2017 (hereinafter the "079 PCT"), which is incorporated herein by reference in its entirety. The present disclosure adds to and expands upon the "sudden unexpected death" disclosures associated with FIGS. 16-20 of the 079 PCT, with specific application to sudden unexpected death in epilepsy (SUDEP) and sudden infant death syndrome (SIDS).

Gastroesophageal reflux disease (GERD) is a common cause of laryngospasm. A closed-loop reflex induces laryngospasm when stomach acid rises into the larynx, protecting the sensitive vocal tissue from damage. The exact cause of acid movement is unknown, and may vary from patient to patient, but both the lower esophageal sphincter (LES) and upper esophageal sphincter (UES) are insufficiently closed, allowing acid to move up from the stomach into the larynx. Chemoreceptors innervated by both the superior laryngeal nerves (SLNs) and recurrent laryngeal nerves (RLNs) can induce laryngospasm. GERD symptoms often occur at night, when acid can more easily move up the esophagus when the subject is in the prone position because gravity no longer draws the acid down into the stomach. Similarly, most SUDEP cases occur at night while the patient is asleep in the prone position, and nighttime seizures increase the risk of SUDEP. Epilepsy and GERD share a statistically significant comorbidity. Increased RLN firing has been demonstrated during seizure, which has been attributed the sudden laryngospasm.

The present disclosure relates to preventing acid reflux induced laryngospasm based on an alternative theory and includes several solutions. The RLN, SLN, and other vagal tracts innervate both the LES and the UES. One possible explanation for the observed laryngospasm is that malfunctioning vagal tracts could relax the UES and LES during seizures, increase the production of acid mediated by the sub-diaphragmatic gastric branch of the vagus, or both, allowing acid to move up from the stomach and into the larynx, triggering laryngospasm. In acid-induced laryngospasm during sleep, the patient normally wakes up and sits up, allowing acid to move back down the esophagus with gravity, and the larynx to relax. During a seizure, the patient remains unconscious, and the laryngospasm may continue until death.

Figure 2:
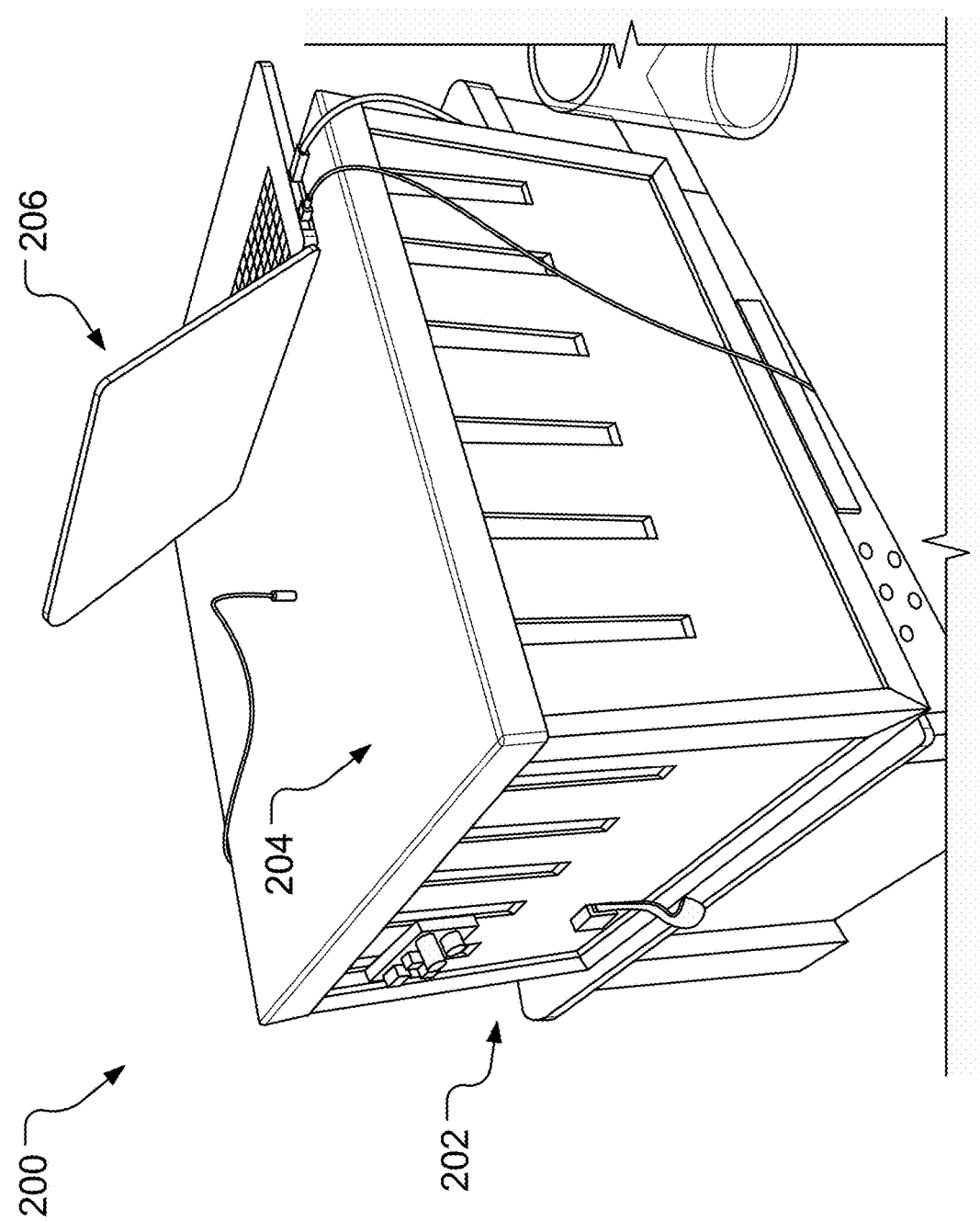
FIG. 2 is a schematic diagram of a monitoring system, in accordance with some embodiments provided herein.

To test this mechanism, a series of tests were performed on rats using a monitoring system 200 shown in FIG. 2, which is of the type shown and described with respect to FIGS. 71-72 of the 079 PCT. The monitoring system 200 can include a base station 202, a powered animal environment 204, and a user interface 206.

The pH in the lower and upper esophagus of rats was monitored during seizures to determine if there was any acid movement and, if so, the kinetics of that movement. A urethane-KA rat model was employed with a small-scale pH sensor using an antimony pH electrode and silver silver-chloride reference electrode. After discovering acid, another set of experiments was performed with the esophagus blocked to confirm that acid was the cause of fatal laryngospasm. Finally, increased production of stomach acid during seizures was confirmed.

Figure 3A:
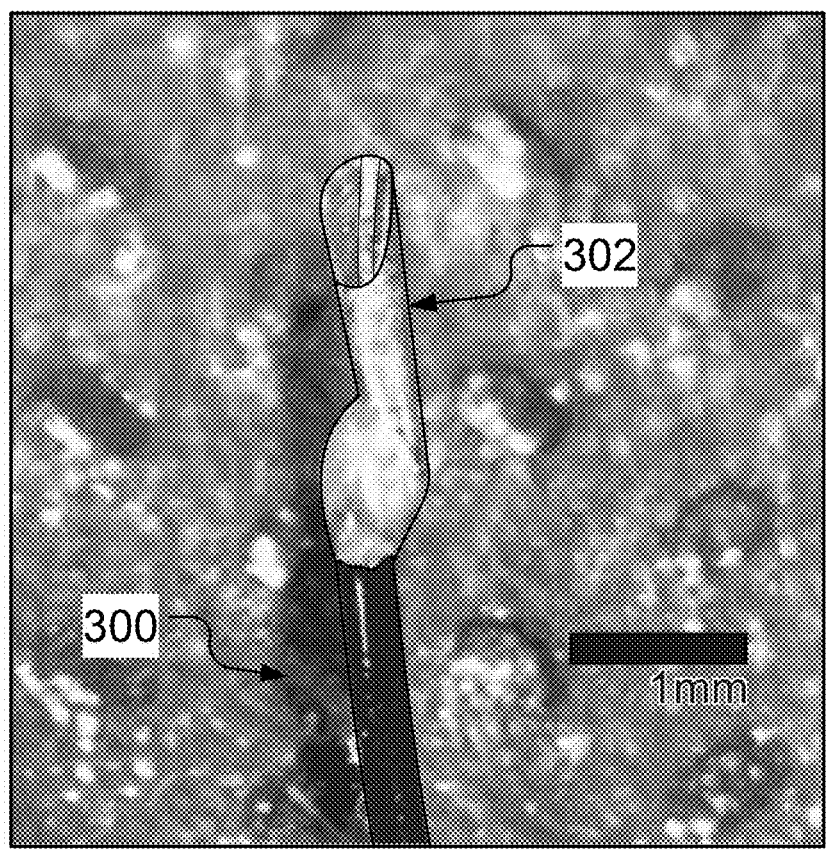
FIGS. 3A-3C show a catheter system, in accordance with some embodiments provided herein.
Figure 3B:
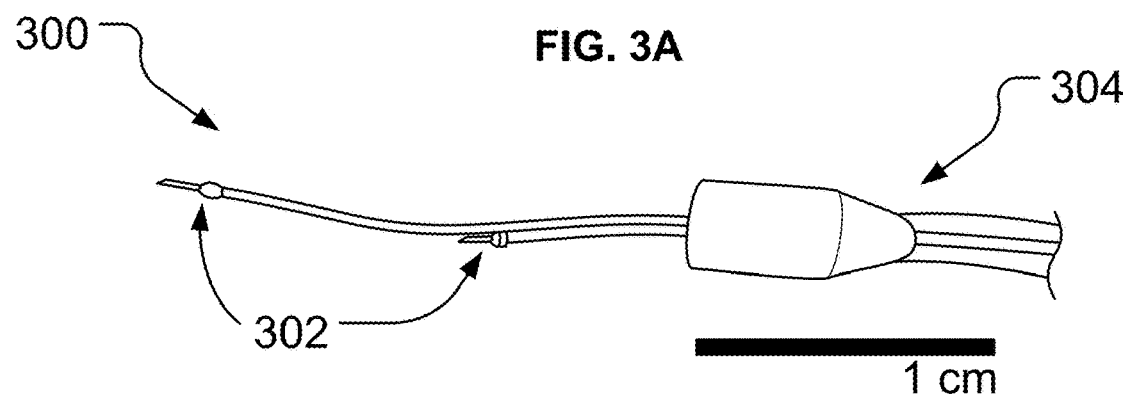
Figure 3C:
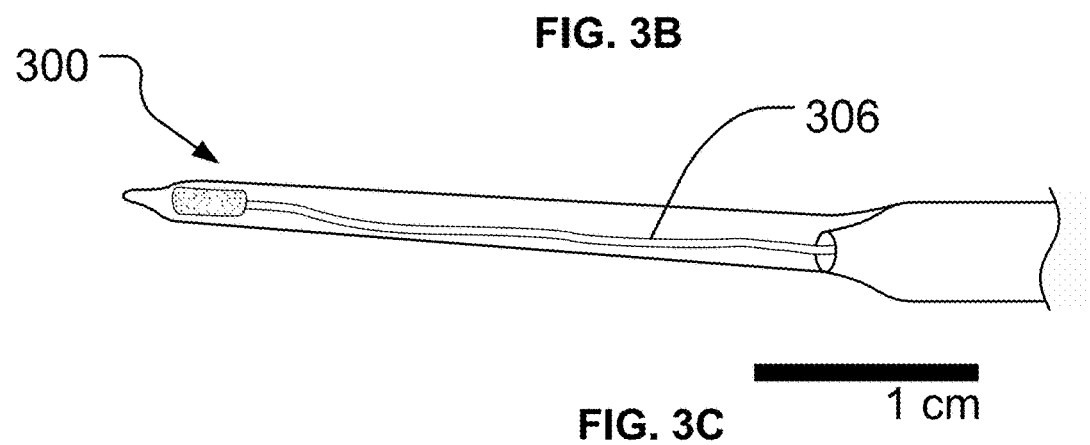

First Methods:

The experiments were performed using the catheter system 300, shown in FIGS. 3A-3C, including antimony electrodes 302 for monitoring acid movement over time, a delivery tube 304 for delivering experiment-specific fluids into the larynx of the test subjects (e.g., acid or saline), and a balloon for esophageal blocking as will be described in greater detail below. FIG. 3A is a close-up image of the antimony pH electrodes 302 used in experiments. FIG. 3B shows two antimony pH electrodes 302 for monitoring acid movement over time, along with the catheter used for the delivery of specified fluid during the experiments (e.g., acid or saline). In some embodiments, the catheter 300 can be a modified feeding tube. FIG. 3C shows the silver silver-chloride reference electrode 306.

Antimony Electrode:

The pH electrode 302 was constructed of elemental antimony. Antimony tips were drawn in glass capillary tubes. Tips were broken and extracted from the capillaries and attached to insulated copper wire with a silver conductive epoxy. Electrodes were then insulated with Loctite epoxy. This construction allowed the electrode to be thin, at most 0.7 mm in diameter, and highly flexible. Electrodes were calibrated in a Tris buffer system vs. a traditional glass electrode. In later experiments, two antimony electrodes were attached via epoxy with 1-2 cm spacing to measure the progress of acid up the esophagus. Combined electrodes were less than 1.0 mm in diameter at the widest point.

Reference Electrode:

Silver silver-chloride reference electrodes were constructed using silicone adhesive and Loctite to seal, and with a wider junction to prevent clogging by tissue in vivo.

Esophageal Blocking:

The catheter system 300 was constructed using a latex balloon and polyethylene tubing 304 to fit in the rat esophagus. A 26-gauge needle was cut from its housing and blunted to form a metal tube. The tube was sealed on one end to a polyethene tube connected to a syringe filled with water, connected to a pressure sensor. The pressure sensor allowed for verification that the balloon remained inflated for the entire experiment. Connected to the other end of the metal tube was a latex balloon, sealed with silk suture and Loctite. When deflated the balloon was <3 mm in diameter, and when fully inflated it could reach >7 mm.

Other Measures:

Animal respiration was monitored with a nasal thermocouple. Heart rate and $SpO_2$ levels were monitored via a pulse oximeter. Animal temperature was maintained via a hot water heating pad or a rectal thermometer and Harvard heating apparatus. pH data was filtered using a simple low pass filter on an AD623AN instrumentation amplifier with G=3 Hz and Gain=2. Thermocouple data was filtered and amplified using a P511 AC amplifier, pass 0.3-100 Hz, Gain=20,000. Data was collected via a NI-DAQ USB 6434 and processed in MATLAB.

Figure 4:
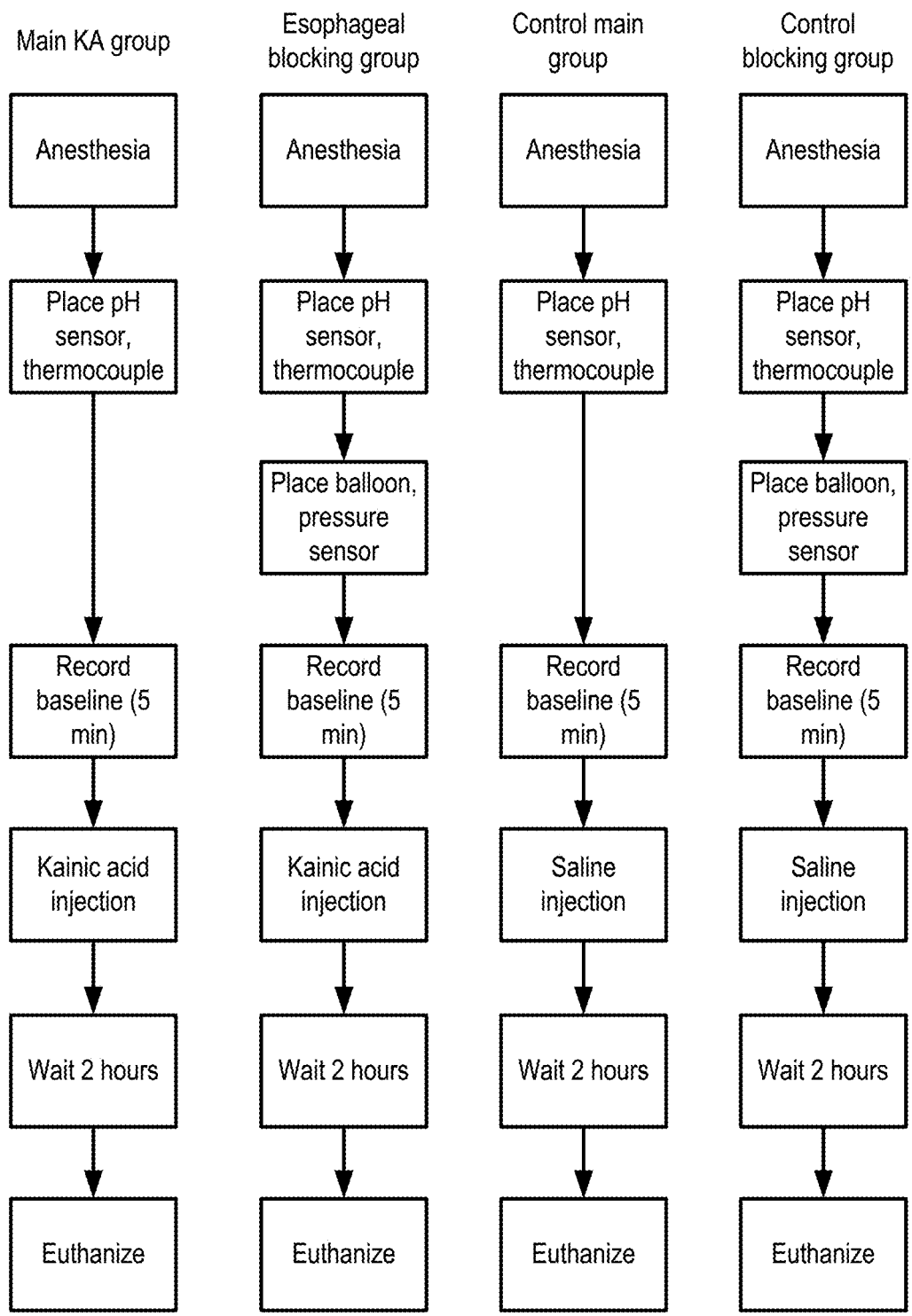
FIG. 4 is a series of flowcharts showing processes for carrying out experiments, in accordance with some embodiments provided herein.

Experiment Design:

The experiments were designed and carried out according to the protocols set forth in FIG. 4.

Experiment Set-Up:

Before and after all experiments, the pH sensor was calibrated in Tris buffers at 7.2 and 2.2 to verify accuracy. All procedures were approved by the Purdue Animal Care and Use Committee. Female Long Evans rats (228 g-327 g, Envigo) were anesthetized with urethane (1.5 g/kg IP). When blocking the esophagus, the balloon catheter was inserted first. The balloon catheter was inserted down the esophagus until met with resistance at the LES. In early experiments, it was determined that the LES is a very strong structure and can be used reliably for electrode placement. The balloon was retracted slightly, to prevent it from pushing the LES open when inflated. The balloon was then inflated with water until there was positive pressure.

The pH electrode was delivered to the esophagus using a modified feeding tube. The tube was pushed into the esophagus until met with resistance at the LES or the balloon. The feeding tube was retracted slightly to ensure the electrode was not placed inside the LES or placed contacting the balloon. The electrode was then placed, and the feeding tube removed. The reference electrode was placed in the subcutaneous space near the right shoulder and the junction kept moist with periodic saline injections throughout the experiment. Baseline data was recorded for at least 5 min. Seizures were induced with kainic acid at a standard dose of 10 mg/kg, however dosing was adjusted 60%-115% of the standard dose, depending on the age of the KA (fresh KA is much stronger). Further, if animals did not exhibit signs of seizure activity after the initial dose, they were given another dose, up to a total of 140% the standard dose. After KA injection, data was collected for 2 hours before euthanasia. However, if the animal experienced a pH drop in the esophagus, then an additional 30 minutes were added before euthanasia, to potentially observe sudden death. In all groups, after death, the pH was measured in the esophagus, and then the stomach, to verify that any acid measurement during the experiment was reasonable based on the stomach pH. Animals were prone for all experiments.

Experimental Groups:

As set forth in FIG. 4, the experiment included a total of 21 animals in three groups.

In the main experimental group (11/21) animals received kainic acid and pH monitoring. In the esophageal blocking group (7/21) the balloon was placed before the pH sensor was inserted, and animals received the kainic acid injection. The pH sensor was used to verify that blocking was successful, and no acid moved past the balloon. In the control group animals received saline injections. The control group included both main group controls (2/21) and balloon group controls (1/21).

Cause of Death Classification:

The animals were separated into groups based on the manner in which they died. Death classification primarily focusing on the breathing pattern. KA-induced seizures can result in different mechanisms of death. The mechanism of interest, sudden death, is characterized by a respiration rate much faster than baseline (60-80/min vs 200+/min). The waveform has rapid, shallow gasping interrupted by sharp breaths. This pattern can include transient apneas which were classified as breathing cessation lasting at least 5 seconds. Breathing will immediately cease just prior to death with the animal's chest still moving (i.e., diaphragm contractions), as if attempting to breathe. The second mechanism involves a gradual slowing of breathing, typically without apnea, until death. Breathing will be slower than baseline (60-80/min vs 24/min) and decrease continually until death. The waveform has sharp intake with gradually slowing exhalation. The animal's chest will not be moving at death (i.e., no diaphragm contractions). For euthanasia, breathing will stabilize to near-baseline rate and waveform before stopping. Other death categories will be addressed later.

Results:

Group 1—KA Injection, No Esophageal Obstruction (11 Animals)

Sudden Death:

In 4 experiments, breathing patterns and seizure activity that was observed is consistent with sudden death. The animals initially presented with respiration slower than baseline, however they quickly recovered, and demonstrated rapid breathing with shallow gasping and sharp breaths. These animals displayed obvious signs of seizure activity, including bulging eyes and occasional tail twitching. Three of these animals experienced transient apneas, some lasting as long as 20 seconds. In all cases the animals' chests were moving after airflow ceased, indicating diaphragm contractions and obstructive laryngospasm as the cause of death. All four of these animals experienced a large pH drop in the esophagus from pH 7 to pH 2 preceding sudden death. The time from pH drop to death ranged from 2 minutes to 81 minutes, with an average of 35 minutes. In two cases the pH drop was fast, occurring over a period of several seconds. In these cases, the lower and upper pH electrodes had very little delay in their respective pH drops indicating that the acid was moving up the esophagus quickly and predicting the observed rapid onset of spasm and subsequent death. In two cases the pH drop was slower, occurring over >10 minutes. In these cases, the lag between the two pH electrodes was several minutes, indicating that the acid was moving up the esophagus slowly and predicting the observed slow onset of spasm and subsequent death. pH drops in the lower electrode occurred an average of 45 minutes after KA injection. Three of these animals died within the 2-hour experiment window. One animal died during the extension allowed for acid, at 2 hours 2 minutes after KA injection. The respiration and pH from one of these animals can be seen in FIG. 5.

Figure 5:
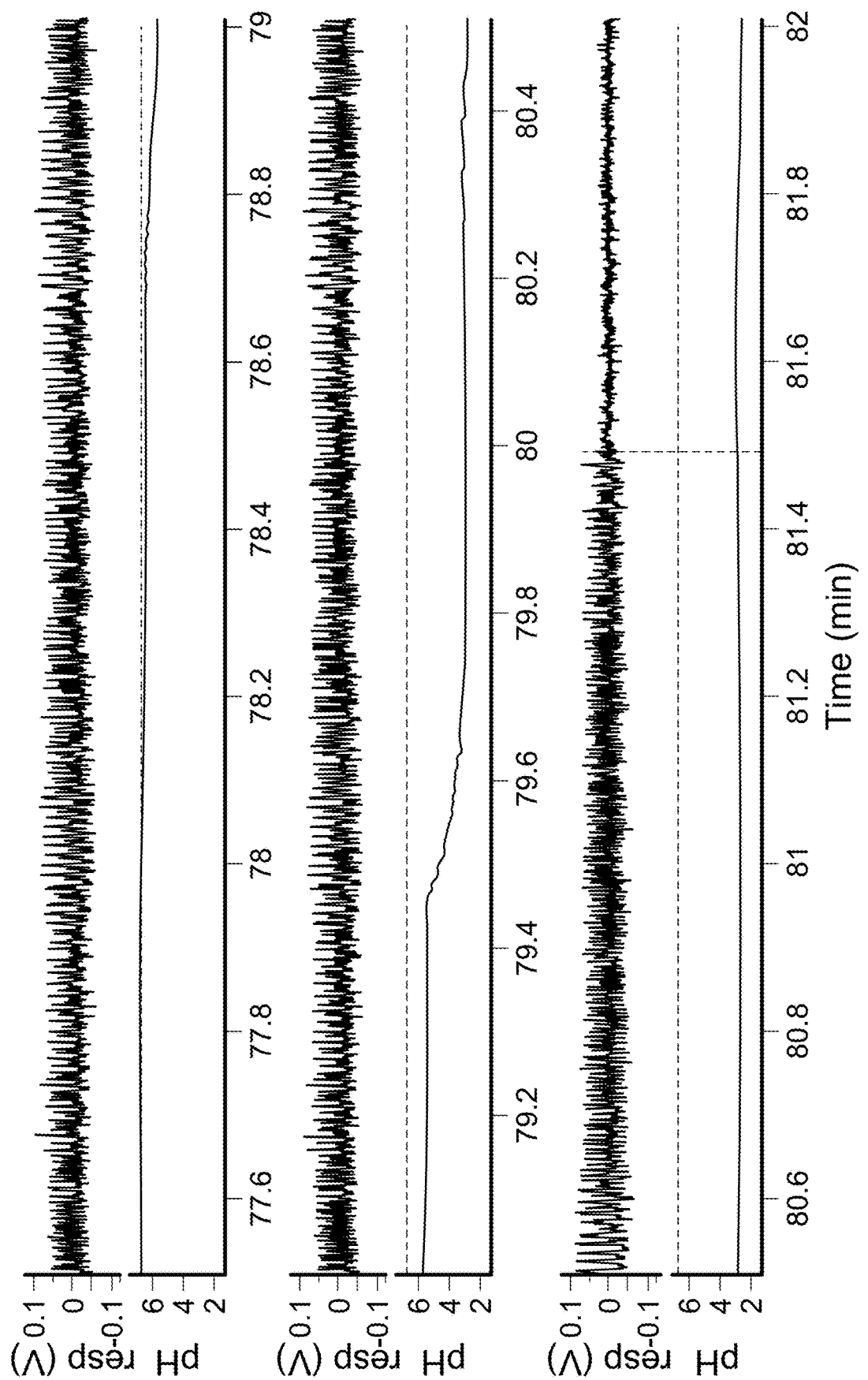
FIG. 5 illustrates respiration data and pH data from an animal during experimentation, just before death.

FIG. 5 illustrates respiration data (top) and pH data (bottom) from an animal just before sudden death. Horizontal dotted lines indicate baseline pH. The vertical dotted line indicates the time of death. Note that pH drops slightly starting at 78.8 minutes and drops again sharply at 79.5 minutes. The time between this pH drop and death is ~90 seconds. This animal was still moving its chest after airflow cessation, suggesting obstructive laryngospasm as the cause of death.

Slow Breathing:

One animal died with extremely slow breathing. Breathing slowed after KA injection and never recovered, gradually slowing until the animal died. There was no pH change, no transient apnea, and no evidence of attempted respiration during final apnea. Death occurred 60 minutes after KA injection. The breathing patterns are consistent with strong seizure activity induced by high KA dosing and status epilepticus.

Euthanized Animals:

Three animals were euthanized at the time limit per procedure. Two of these animals experienced a pH change, but less significant changes in breathing. Both pH changes were slow, occurring over tens of minutes. In both cases the animals survived past the extension window. One animal saw no pH change and displayed minimal signs of seizure activity.

Indeterminate:

Indeterminate animals displayed behaviors fitting into more than one category. One animal observed a sharp pH change and died 30 minutes later, but the breathing pattern was not consistent with the sudden death animals. The breathing rate was much slower than baseline (60/min vs 12/min) but was stable for 20 min before suddenly stopping. In all other cases of slower-than-baseline breathing, respiration continually declined, and never stabilized. There was no apparent effort to breathe during the final apnea. The second animal in this category showed slower than baseline breathing (80/min vs 48/min) that was stable for over an hour. At the 2-hour mark the animal was euthanized, as there was no acid detected. 5 minutes after euthanasia was injected there was a sudden, sharp pH drop from 7 to 2, indicating a possible failure in the esophageal sphincter resulting from the euthanasia rather than induced epilepsy. Two minutes later the animal died suddenly. There was no change in breathing pattern from before euthanasia injection until sudden death, which is atypical. For these reasons, both of these animals were classified as indeterminate.

Other:

In one animal strong seizure activity 30 seconds after KA injection was observed, transient apneas 90 seconds after injection, and the animal died 4 minutes after injection. There was no pH change, and the breathing pattern was constantly changing. Most animals will show signs of seizure activity 15-45 minutes after KA injection. It is unclear why this animal had such a strong reaction, and its death was unlike other categories, so it was placed in its own category.

Group 2—KA Injection, Esophageal Obstruction (7 Animals)

Slow Breathing:

Three animals had breathing significantly slower than baseline, which gradually slowed until death. None of these animals had acid in the esophagus after death. No animals experienced transient apneas. In two cases, it was observed that animals were making a whistling sound during inhalation, so the pressure in the balloon was decreased, and the whistling stopped.

Euthanasia:

Four animals survived until the 2-hour mark, at which point they were euthanized. Three animals had behavior similar to animals that suddenly died. They all had transient apneas, some lasting as long as 20 seconds. Their respiration waveforms had rapid gasps with sharp breaths. All three of the animals had acid in the esophagus, below the balloon, which was measured after death. All three of the animals that were initially observed with whistling sounds during inhalation, which was relieved by decreasing the water in the balloon. In one case there was a small amount of acid leakage past the balloon, enough that only the lower electrode detected it. In one case there was another acid leakage with enough acid to be detected on both electrodes. In both cases the acid leakage occurred near the end of the experiment and did not cause laryngospasm. The last animal in this category had no pH change and no transient apnea. This animal's behavior was similar to the other euthanized animals from the main group.

Group 3—Control (3 Animals)

Figure 6:
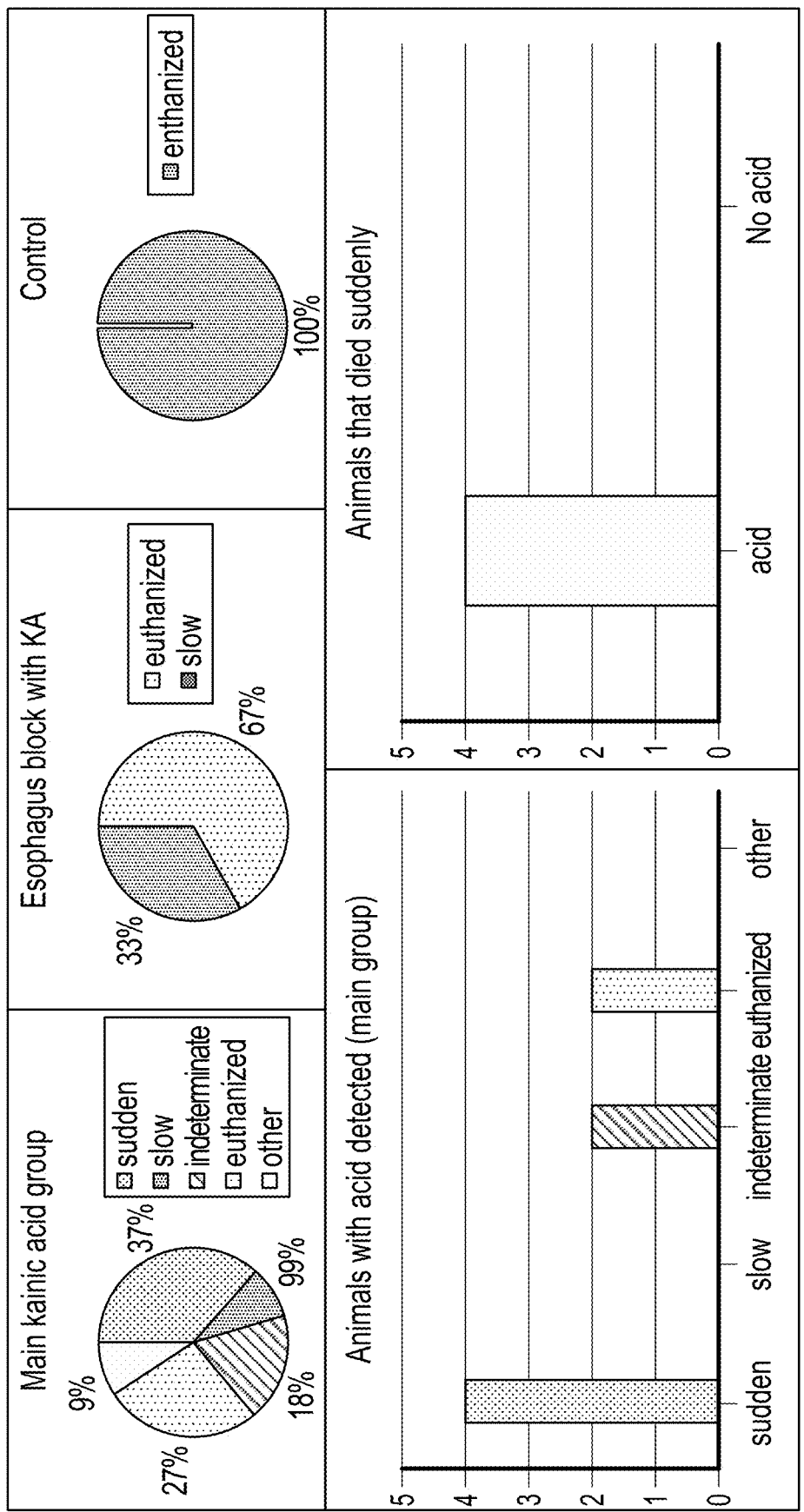
FIG. 6 shows various charts of experimental results.

Euthanasia:

All animals survived until the 2-hour mark and were then euthanized. No animal experienced a pH changed, and none demonstrated breathing pattern changes or transient apneas. There was no difference between balloon and non-balloon animals. FIG. 6 illustrates these results.

Timeline of Response:

Animals displayed a relatively consistent response to KA with several critical branching points. Approximately 10 minutes after KA injection animals would demonstrate alterations in breathing that varied significantly. Approximately 25 minutes after KA, animals would either have stabilized into faster than baseline or slower than baseline breathing. Faster breathing animals may experience transient apneas. Approximately 45 minutes after KA injection, some of the slower-than-baseline animals would recover, and transition to fast breathing, sometimes with transient apneas. Animals with fast breathing may experience a pH drop around this time. If animals with slow breathing did not recover by 60 minutes after KA injection, then they would never recover, and respiration would slow until death. If an animal had fast breathing 60 minutes after KA injection, then they would continue this trend, experiencing transient apnea, pH drop, and sudden death in some cases, and surviving until the time limit in others. When animals were having strong seizures, it was observed due to their eyes bulging, whiskers/tail twitching, and occasional limb movement. It was observed that transient apneas tended to cluster, occurring several times within a few minutes, and then not again for many minutes. These transient apnea clusters usually occurred during strong seizure activity. Sudden death usually occurred outside of strong seizures.

Other Observations:

Several times after death from seizures a pool of liquid was observed at the animal's mouth, which was never present in control animals. Twice, the pH of this pool of liquid was measured and it was found to be very low (about pH 2). Once, the pH was measured to be about 4. In all cases the pool of liquid was present after death, but before any of the sensors had been pulled out of the esophagus. In nearly all of the KA experiments, the animals would repeatedly lift their heads for a moment, looking almost like a hiccup. There was initial concern that this behavior was a reflex to the presence of the sensors in the throat, however this behavior was never observed in the control animals. In two animals a sharp pH change was observed after euthanasia injection. This acid movement was never observed in control animals.

Analysis:

1. Acid as a necessary component of sudden death:

Sudden death occurred in 4/11 animals in the main group, and in 0/7 animals in the esophageal blocking group. These groups are significantly different from one another (p=0.035, z-test). The groups are still significantly different when comparing animals with transient apnea, 3/5 vs 0/3 (p=0.045, z-test), animals with acid detected, 4/8 vs 0/3 (p=0.062, z-test) and animals with both transient apnea and acid, 3/4 vs 0/3 (p=0.024, z-test).

2. Increased stomach acid volume as a potential component of subsequent acid reflux 3. Seizure as a necessary component of acid reflux and sudden death 4. Transient apnea as a predictor for sudden death:

For the main group, 5 of 11 animals showed transient apnea. Three of these animals died suddenly, one was euthanized, and one was the aforementioned "other" death. While this prediction is not statistically significant, (p=0.068, z-test), it is not certain that the euthanized animal would not have died suddenly, and the other animal was an outlier. Transient apnea was present in 75% of sudden deaths and occurred many minutes before death.

Discussion:

It was observed that acid in the esophagus is 100% correlated with sudden death. Further, when acid is prevented from moving up the esophagus, sudden deaths cease indicating causation. Excess stomach acid production was observed during seizures, to the point at which acid contents can move all the way into the mouth and out of the animal. These observations are strong evidence that acid is the primary trigger of laryngospasm, and subsequent death in the KA model. It was also observed that transient apneas occur in most cases of sudden death and may be a useful predictor to prevent them. It was observed that animals had varying behavior in response to KA, but these behaviors clustered neatly into the different death categories, suggesting that there are multiple mechanisms involved.

Based on these observations, the death categories set forth herein are useful not just for categorizing SUDEP, but also for categorizing types of KA-induced seizures. By the end of the experiments, how an animal would die based on its response to KA was able to be predicted according to the flow chart of FIG. 4. Respiratory depression appears to be associated with the strong seizures that start the response to KA, while obstructive laryngospasm appears to be associated with the shorter seizures that follow. A strong initial seizure response to KA was associated with continuous seizure activity (status epilepticus). It is proposed that death caused by gradual respiratory depression is similar that observed in status epilepticus, rather than that caused by acid reflux and laryngospasm, leading to SUDEP.

The presence of acid in the esophagus and mouth is extraordinary because rats cannot normally vomit. They lack the musculature to produce retching, and acid movement does not occur, even when given emetic agents. In humans there is constantly acid in the esophagus, and even regularly appearing in the larynx in some cases. GERD and other reflux disorders are not gauged by the presence of acid, but by the proportion of time that the structures have a very low pH. Normal patients will have esophageal pH<4 approximately 5% of the time. Low pH is expected, but this only causes problems when it becomes frequent or moves especially high, such as into the pharynx. This is not the case for rats, in which the presence of any acid at all is abnormal.

Time Delay Between Acid and Laryngospasm:

In one case the animal died very shortly after the pH change, but in the other cases it took tens of minutes. In a healthy animal, laryngospasm should occur instantaneously once acid has reached the larynx. There are several reasons why the delay might exist. First, pH was recorded at the bottom of the esophagus, so it is uncertain when the acid actually reached the larynx. The UES could not be felt when inserting the electrodes, so there was not an appropriate marker to ensure that the electrodes were placed correctly and consistently. Second, there appear to be different mechanisms of acid movement. In some experiments the pH change was a slow, consistent drop, while in others it was sudden and sharp. In one experiment, both phenomena were observed: one on the lower electrode, and the other on the upper electrode. It is uncertain how long it took for acid to move from the electrodes toward the bottom of the esophagus to the UES and larynx. Finally, the pH sensor itself may be blocking or slowing acid movement.

The Kainic Acid Model:

The KA model is useful because it can produce temporal lobe epilepsy like seizures in an acute setting. However, the KA model does not, by definition, produce SUDEP-like seizures, as it induces seizures in an otherwise healthy brain. The KA model also has some variability in the mechanisms of death. Significant variability between animals with the same dosing was observed. Some animals showed no seizure activity, some showed transient apnea, some respiratory depression, etc. It is uncertain which of these behaviors is SUDEP-like, and which are not. The KA model is useful up to a point, but these results must still be proven in a chronic model.

Mechanism:

It is believed that stomach acid induced laryngospasm may be a primary mechanism behind SUDEP. It was hypothesized that seizure activity causes relaxation of the LES and UES, concurrently with possible overproduction of stomach acid, which combine to force stomach acid up the esophagus and into the pharynx. Once in the pharynx, the acid triggers an obstructive laryngospasm, from which the patient is unable to recover.

Overproduction of Stomach Acid:

Another possible mechanism is the large quantity of stomach acid that may be produced during vagal nerve stimulation. During one of our balloon experiments, a sharp drop in pH above the balloon was observed towards the end of the experiment. During seizure activity, the vagus nerve can have pathological activity, which could result in the overproduction of stomach acid.

Figure 7A:
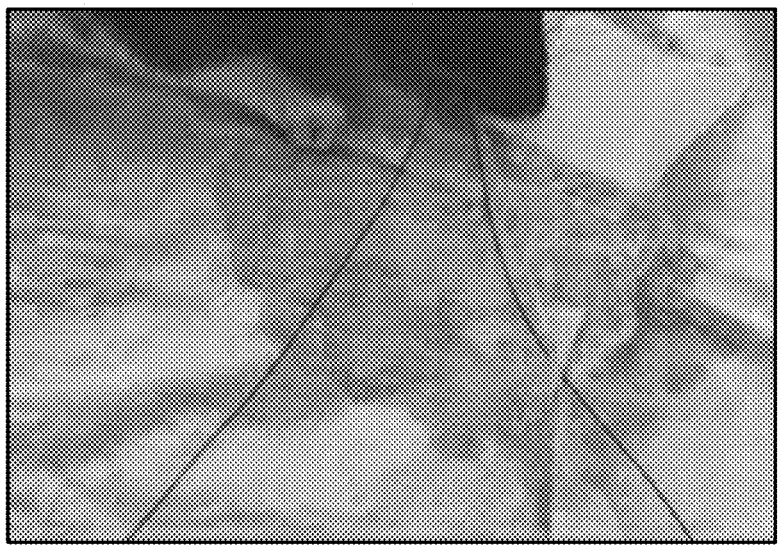
FIGS. 7A-7C evidence acid movement out of the mouth.
Figure 7B:
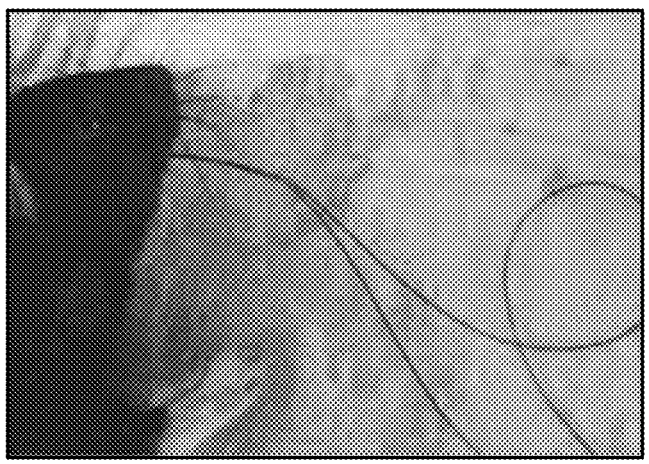
Figure 7C:
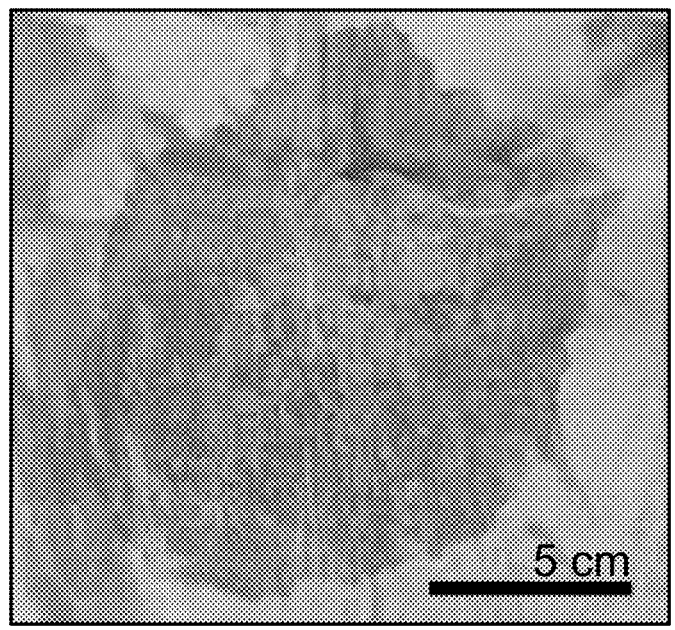

FIGS. 7A-7C supports the notion that vagus nerve stimulation may cause the overproduction of stomach acid. More specifically, FIGS. 7A-7C evidence acid movement out of mouth. FIG. 7A shows an animal with fluid at the mouth before any electrodes have been removed. The balloon was still functional and fully inflated, but still some acid had pushed past. FIGS. 7B and 7C show fluid after the experiment (including visible food particles), which was measured to have a very low pH (about pH 2). When removing the balloon from the animal, a large amount of fluid escaped the animal's mouth, making a large stain on the surgical surface, about 6 cm by 8 cm. It was believed that a large amount of stomach acid was produced, increasing the pressure in the stomach, eventually forcing some stomach acid past the balloon. Vagus nerve activity can trigger the production of stomach acid, and overproduction of acid may be a major factor in acid movement.

These experiments may provide insight into other mechanisms of sudden death. Sudden infant death syndrome (SIDS), kills approximately 2,000 infants every year in the US. The risk for SIDS can be reduced by placing a baby supine, not prone, to sleep. The supine position places pressure on the esophagus and may impede acid movement. Like SUDEP, SIDS often occurs at night, and infants would not be able to sit up and clear acid if it entered their larynx the way adults do. It is possible that the mechanism for SIDS is related to acid induced laryngospasm as well. There is evidence that SIDS is preceded by laryngeal inflammation, which may be caused by stomach acid.

To date there is early evidence in support, and no evidence to contradict the hypothesis that SUDEP is caused by stomach acid-induced laryngospasm. This mechanism is important to explore because several anti-epileptic drugs, such as Acetazolamide, Carbamazepine, Clobazam, Ethosuximide, Gabapentin, Levetiracetam, and more have side effects that increase stomach acid movement into the esophagus. While certainly beneficial for most patients, there may be some for whom these drugs introduce a rare but possibly lethal risk.

It has been demonstrated that sudden death due to laryngospasm in the kainic acid model of epilepsy is always preceded by a significant pH drop in the esophagus. Further, that eliminating this pH drop also eliminates sudden death. This knowledge may inform future research into sudden death in epilepsy and may contribute to the presented hypothesis. This mechanism may be important in other mechanisms of sudden death.

Second Methods:

Experimental Groups:

Seven experimental groups were studied. Groups 1-5 follow a similar surgical procedure appropriate for statistical comparisons, while Groups 6-7 follow separate procedures and are presented for observations and preliminary findings.

All experiments are acute with anesthesia. In Groups 1-5 esophageal pH, electrocorticography (ECoG) activity, and respiration via thermocouple was recorded for all animals (henceforth referred to as "standard measures"). After death the stomach contents were removed.

Group 1 (n=6): Kainic acid—these animals had their gastric nerve exposed, but not severed, to act as a partial control for Group 2. They received standard measures and seizures were induced with kainic acid (KA).

Group 2 (n=7): Gastric sever—these animals had the gastric branch of the vagus nerve severed. They received standard measures, and seizures were induced with KA.

Group 3 (n=3): Gastric sever controls—these animals had the gastric nerve severed but received a saline injection instead of KA. All standard measures were performed.

Group 4 (n=7): Fasted KA—these animals had food and water withheld for at least 12 hours prior to the start of the experiment. Additional subcutaneous saline was given to restore animals to normal hydration at the start of surgical procedures. They received standard measures and seizures were induced with KA.

Group 5 (n=3): Fasted controls—these animals are similar to Group 4 but received a saline injection instead of KA. All standard measures were performed.

Group 6 (n=7): Laryngeal stimulation—in these animals the recurrent laryngeal nerves (RLNs) were electrically stimulated to reopen the larynx following acute induced laryngospasm. One animal was used as a control, and no stimulation was applied, to observe the normal laryngospasm response. In these animals respiration was measured with a thermocouple.

Group 7 (n=7): Gastric nerve blocking—continuous electrical blocking was attempted on the gastric nerve to recreate the results of Group 2 without permanently damaging the nerve. All standard measures were performed, and seizures were induced with KA.

Animal Procedures

Electrocorticography (ECoG) data from over the dorsal hippocampus was obtained by placing bone screws at bregma AP—2.5 mm, lateral—2.0 mm (measurement electrode), and bregma AP+0.5 mm, lateral—2.0 mm (reference electrode). pH electrodes were placed at the bottom of the esophagus by placing the electrodes inside a modified feeding tube, pushing the feeding tube and electrodes to the lower esophageal sphincter, retracting approximately 3 mm, and removing the tube. The pH electrodes were taped outside the mouth and the distance was measured from the mouth throughout the experiment to ensure the electrodes did not significantly migrate and were not swallowed by the animal. Reference silver/silver-chloride electrodes were placed in the subcutaneous space on the right dorsal of the animal, just caudal to the shoulder, and periodically injected saline to keep the reference moist. Respiration was measured via a thermocouple placed near or just inside the nares. Excess mucous (if present) was removed by wiping the nose with a cotton swab. Animals were grounded from a power supply through a subcutaneous hypodermic needle. Baseline physiological measures were collected for at least 5 min before injections. Kainic acid was injected (10 mg/kg i.p.) to induce seizures, while control animals received an equivalent volume of saline.

The KA dose was reduced to 80% for fasted animals, as they exhibited signs of KA overdosing which include, respiration significantly slower than baseline and severe gradual drop in blood oxygen saturation, which was approximated in the experiments by observing severe cyanosis at the hind- and fore-paws. Data was collected for at least two hours. An additional 30 minutes of observation was added if there was a strong reflux of acid (pH<3 on both pH electrodes), or if the animal displayed signs of respiratory distress and appeared to be close to dying. Animals were then euthanized with phenytoin/pentobarbital (45 mg/351 mg) and the stomach was promptly removed. Stomach size, pressure, and color were observed, and the stomach contents were removed into a conical tube.

Gastric Vagotomy:

The ventral aspect of the rat was shaved from the caudal edge of the ribcage to approximately 1 cm rostral of the rat's knees. With the animal supine, an incision was made approximately 0.5 cm left of midline, starting in line with the apex of the xiphoid process and extending approximately 3 cm caudally. This incision went through both the skin and abdominal wall. The right medial lobe, right lateral lobe, and quadrate lobe of the liver were reflected rostrally, and the hepatogastric ligament was cut. The preventricular part of the papillary process was rostrally reflected, allowing the esophagus to be visualized. The left vagus nerve, visible on the ventral side of the esophagus, was used as a landmark, and followed it rostrally until the bifurcation with the hepatic branch was visible. This is the end of the procedure for animals in Group 1. In Groups 2 & 3, the gastric branch (2-3 mm caudal to the hepatic branch) was then lifted from the esophagus with a microdissection hook and severed using an electric cautery.

pH Measurement:

pH measurement was previously described. Antimony pH electrodes were constructed by melting and drawing antimony in glass tubes. pH and reference electrodes were calibrated in pH 7.2 and 2.2 Tris buffers to verify accuracy, and compared to a traditional glass electrode. In animals with pH measurement two pH electrodes were placed—one at the bottom of the esophagus and one 1 cm rostral, to measure the progress of acid over time.

Stomach Contents Analysis:

The stomachs were removed shortly after death and manually removed the contents into test tubes. The empty stomachs were weighed to verify that they were, indeed, empty. All stomach content samples were frozen shortly after collection. The samples were thawed in a water bath at room temperature for approximately three hours before centrifuging them—2500 rpm for 5 min, followed by 3000 rpm for 5 min—to separate the majority of liquid and solid contents. The full samples were weighed, the liquid contents were discarded, and samples were left in a lab hood for three days to fully evaporate remaining liquid. The samples were weighed again to determine the total solid and liquid mass in the stomachs.

Acute Induction of Laryngospasm:

For animals in Group 6 acute laryngospasm was induced by placing acid directly on the larynx. These animals also received butorphanol (0.5-2 mg/kg s.c.) in addition to urethane anesthesia.

An acidic biological buffer was created using Tris titrated with HCl to a pH of 1.6 to approximate stomach acid. Using a 2.7 mm, 30 degree Dyonics 4130 video laryngoscope and a custom 3D printed cannula, the larynx was visualized and record using a GoPro Hero5 Black, modified by Back-Bone. Using a catheter, 0.1 mL of the simulated acid was injected onto the larynx to immediately trigger laryngospasm. It was attempted to stimulate the laryngeal nerves to open the larynx. To accommodate the laryngoscope, these animals were secured supine in a stereotaxic frame. In one control experiment, laryngospasm was induced without placing the laryngeal nerve cuff. In this experiment, acid was placed on the larynx to observe a normal laryngospasm response.

Laryngeal Stimulation:

A large cuff electrode was constructed to fit around the trachea. A 90/10 Pt—Ir wire with OD 75 µm was threaded through a split silicone cuff with an inner diameter of 3 mm. The wire was threaded parallel to the nerve to increase surface area. The cuff electrode was placed around entire trachea in order to stimulate all laryngeal nerves. In some experiments, the laryngeal nerves were severed on one or both sides to confirm that the stimulation was affecting the nerves directly, not the surrounding muscles. An alternating-phase stimulation of 500 µA with a pulse width of 100 µs and a pulse repeat time of 500 µs was applied, which was sufficient to hold the larynx open. During these experiments the incision was kept moist with saline and was covered with cling wrap to prevent it from drying out.

Electrical Blocking:

In Group 7 a continuous electrical blocking stimulation was applied to the gastric nerve to simulate the effect of severing the nerve in Group 2, but without permanent nerve damage. Before the standard surgical procedures for Groups 1-5, the left cervical vagus nerve and the gastric branch of the left vagus nerve were exposed and cuffed. Cuff electrodes were constructed similar to the laryngeal nerve cuff. The cervical cuff was constructed of the same Pt—Ir wire, with two wires (stim + and stim −) inside a split silicone tube with an inner diameter of 0.64 mm (AM Systems). The gastric cuff was constructed of four Pt—Ir wires (block +, block −, record −, record +) inside a split silicone tube with an inner diameter of 0.51 mm (AM Systems). To verify that the electrical blocking was successful, compound nerve action potentials (CNAPs) were evoked at the cervical cuff and then blocked them at the gastric cuff. CNAPs were evoked with an alternating-phase waveform of 60-150 µA, a pulse width of 250 µs, and a pulse repeat time of 50 ms. CNAPs were then blocked with a continuous square wave between 70%-110% the amplitude of the stimulation waveform and a pulse width of 250-125 µs (a frequency of 2 kHz to 4 kHz). The last 20% of each blocking square pulse was forced to ground to prevent a buildup of charge on the DC blocking capacitor, maintaining charge balance.

Results

Observations from Groups 1-5:

It was observed that animals can have varying responses to KA-induced seizures, with an extended period of seizure activity that can include both periods of extended seizure activity and short, recurring, discrete seizure events with short periods of severe ECoG signal depression. Eighteen of 20 seizing animals in Groups 1-5 saw a marked increase in respiratory rate with a characteristic respiratory pattern that includes rapid shallow gasping with occasional augmented breaths. Animals with this seizure response may also experience transient apneas with no chest movement, acid reflux, followed by sudden obstructive terminal apnea with chest movement. Two of 20 seizing animals in Groups 1-5 animals experienced a different seizure response marked by respiratory depression and cyanosis, severe change in color of the hind- and forepaws was observed. Animals that experienced obstructive apnea had ECoG signals with a greater-than-baseline RMS amplitude (6.4±2.4 dB) until obstructive apnea. Animals that experienced gradual respiratory depression and cyanosis had ECoG signals with equal-to or less-than-baseline RMS amplitude (−1.4±2.7 dB), which gradually decreased until death. Animals that either survive to euthanasia had ECoG signals that are larger than baseline in RMS amplitude (3.9±2.9 dB), and remain stable until terminal apnea, suggesting strong, ongoing cortical seizure activity until death, similar to animals that experience obstructive apnea. An increase in ECoG amplitude in these animals always corresponds to an increase in the power of the signal >30 Hz, which is indicative of seizure activity. These animals also display strong exophthalmos (bulging eyes) and twitching of the whiskers. Conversely, animals that experience gradual respiratory depression have marked cyanosis and an ECoG signal that gradually diminishes over time, suggesting gradual hypoxia until death. Further, these animals rarely exhibit exophthalmos or whisker twitch, have never experienced transient apneas, and have in only one case experienced acid reflux.

Animals that suddenly died have ECoG signals that are much larger than baseline until obstructive apnea and death. Animals that experience respiratory depression have ECoG signals that gradually decline until death.

Sudden Death:

Sudden death was characterized by a seizure response with rapid irregular breathing, occasional transient apnea, exophthalmos, and whisker twitch. In every case, sudden death was preceded by acid reflux into the esophagus. Animals maintained this respiratory pattern until sudden obstructive laryngospasm, during which time respiratory effort was observed, as the chest was still moving, despite a lack of airflow, suggesting obstructive apnea and laryngospasm. In all cases obstructive apnea was terminal. Sudden death was observed in 4/6 animals in Group 1, 0/7 animals in Group 2, 0/3 animals in Group 3, 0/7 animals in Group 4, and 0/3 animals in Group 5. Both severing the gastric nerve (Group 1 vs Group 2) and fasting (Group 1 vs Group 4) significantly reduced the incidence of sudden death ($p=0.012$, $p=0.012$, respectively).

Gradual Respiratory Depression:

Respiratory depression was characterized by a seizure response with gradually slowing respiration and narrowing of ECoG, with marked cyanosis. Respiratory depression generally occurs earlier in the experiment, before the rapid irregular respiration and acid reflux, but in one case it was observed near the end of the experiment, after acid reflux had occurred. Death from gradual respiratory depression was observed in 2/7 animals in Group 4, and none in any other group. In one case there was acid reflux before death. Two of the first 3 animals in Group 4 displayed a seizure response that initially looked similar to respiratory depression—respiration slower than baseline with a narrower ECoG signal, but they eventually recovered to a normal seizure response. Because the first three animals in this group displayed signs of respiratory depression, and one died from it, it was hypothesized that fasting made the animals more susceptible to KA, so the KA dose was lowered from 10 mg/kg to 8 mg/kg for the next four animals, who displayed more typical seizure responses. Incidence of respiratory depression was not significantly different between groups, but this could be due to the low incidence of these types of deaths.

Survival:

All animals that survived to euthanasia displayed the typical seizures response of rapid irregular breathing (or were controls). Survival was observed in 2/6 animals in Group 1, 7/7 animals in Group 2, 3/3 animals in Group 3, 5/7 animals in Group 4, and 3/3 animals in Group 5. Severing the gastric nerve (Group 1 vs Group 2) significantly improved survival ($p=0.012$) but fasting (Group 1 vs Group 4) did not ($p=0.27$).

Acid Reflux:

Acid reflux was characterized by pH<3 on both electrodes. Acid reflux was observed in 6/6 animals in Group 1, 1/7 animals in Group 2, 0/3 animals in Group 3, 2/7 animals in Group 4, and 0/3 animals in Group 5. Both severing the gastric nerve (Group 1 vs Group 2) and fasting (Group 1 vs Group 4) significantly reduced incidence of acid reflux ($p=0.001$, $p=0.008$, respectively).

Stomach Contents:

Stomach contents were collected for all animals in Groups 1-5. The volume of liquid in the stomach was analyzed, which was normalized to animal weight, and reported as a percentage. The liquid ratio was found to be 0.91%±0.38% for Group 1, 0.42%±0.23% for Group 2, 0.18%±0.04% for Group 3, 0.31%±0.11% for Group 4, and 0.17%±0.11% for Group 5. Both severing the gastric nerve (Group 1 vs Group 2) and fasting (Group 1 vs Group 4) significantly reduced the amount of liquid in the stomach ($p=0.015$, $p=0.002$, respectively). These differences are likely greater than the data suggests, as all animals in Group 1 experienced acid reflux, and the amount of liquid that was recovered does not include the contents of the esophagus. Liquid contents from fasting and gastric severing were not significantly different from their controls (Group 2 vs Group 3, $p=0.104$, Group 4 vs Group 5, $p=0.107$); however, that these comparisons may become significant with a much larger sample number, and that fasting and gastric severing reduce some, but not all, of the acid produced.

It was observed that the stomachs of seizing animals often had a large amount of air and had higher internal pressure than the stomachs of non-seizing animals. Initially, it was thought that this air might be produced by the excess acid digesting food in the stomach very quickly, which would generate gas. However, large quantities of air in the stomach of fasted rats was observed, with almost no solid mass in their stomachs. No air was observed in the stomachs of control animals. It was observed that seizing animals would often lift their head during seizures, looking like a hiccup or belch. It is now hypothesized that this behavior is aerophagia (air swallowing), which would explain air.

Acute Laryngospasm Induction (Group 6 Control):

Acid was placed onto the larynx of a control animal to observe a normal acid-induced laryngospasm response. The experiment was repeated 5 times. In each repetition, the animal initially experienced strong laryngospasm for a period of 28-40 seconds. During strong laryngospasm the animal could make infrequent breaths, but the larynx was completely closed for most of this period. The animal made obvious movement in the neck and abdomen, suggesting respiratory effort. Thermocouple data during this time confirms that there was only airflow during the infrequent breaths. Strong laryngospasm would spontaneously end, and the animal would begin a period of labored breathing. Movements in the abdomen were exaggerated compared to normal respiration, and respiration noise was more noticeable. There was an increase in fluid around the larynx, and it appears that the labored breathing was an attempt to clear this fluid from the larynx. Over several minutes, the amount of the fluid around the larynx decreased, and respiration speed and abdominal movement returned to normal. In the first trial, following strong laryngospasm, the glottis blocked view of the laryngoscope, and the animal began breathing through its nose, so there is not good data for this trial, as the thermocouple was placed in the cannula near the mouth. Animals normally breathe through their nose, but in the presence of the laryngoscope they will preferentially breathe through their mouth. In every trial the animal was able to recover from laryngospasm on its own and return to normal breathing after several minutes. Over approximately 75 minutes the animal experienced 5 obstructive apneas and survived, in stark contrast to the seizing animals who experience obstructive apnea under KA.

Laryngeal Stimulation (Group 6):

During normal respiration it was observed that the larynx is almost entirely open during inhalation and is semi-open during exhalation. Waveforms of varying amplitude were applied and it was found that the larynx could be kept in the semi-open position indefinitely by applying the established waveform (500 µA with a pulse width of 100 µs and a pulse repeat time of 500 µs), and that increasing amplitude did not further open the larynx. When held in this semi-open position, the animal was able to breathe normally. After determining this waveform, acid was applied to induce laryngospasm, similar to the control, which immediately closed the larynx. When the stimulation was applied, the larynx could be held in the semi-open position, even in the presence of acid, for as long as the stimulation was maintained. During this time there was airflow through the larynx. If the stimulation was stopped before the animal fully recovered (i.e. before the 28 s period of complete closure observed previously), then it would again experience a strong laryngospasm.

The distance between vocal folds was measured, and the distance was found to be 121 pixels during normal respiration, 28 pixels after laryngospasm but before stimulation, 71 pixels during laryngospasm and while stimulation was on, and 30 pixels during laryngospasm but after stimulation had been stopped. Acid applications were repeated several times for each animal, but after 5 or more acid injections the respiration rate began to slow significantly, and in some cases it was also observed that the respiration sounded wet and ragged. The experiment was terminated at this point, but in two cases animals did not recover, and died. Inspiration of the acid, mucous, and/or saliva into the trachea may have caused respiratory disruption. For three experiments, one or both RLNs were damaged, as there was laryngeal paralysis on the damaged side, even during normal respiration. In 3/3 cases electrical stimulation of these damaged nerves yielded no effect. These experiments suggest that the stimulation was acting on the RLNs directly, not the surrounding muscles. These experiments suggest that laryngeal stimulation can open the larynx in the event of laryngospasm, but that survival is still dependent on the amount of acidic fluid inspired.

Electrical Blocking of the Gastric Nerve (Group 7):

Cuffs were successfully placed on both the gastric and cervical vagus nerves of all animals. When only the stimulation waveform was applied, the evoked CNAP was able to be recorded on the recording cuff. This response showed a clear stimulation threshold, suggesting it is a real CNAP and not a stimulation artefact. The distance between the stimulation and recording cuff was approximately 7 cm, and the response was recorded approximately 25 ms after stimulation, so the velocity of this response was approximately 2.8 m/s, suggesting a B fiber (typically 3.0 m/s or more). When both the stimulation waveform and the blocking waveform were applied, no CNAP response was observed. This response also showed a clear threshold, suggesting that the blocking effect was due to physiological effects, and not masking by extra noise or artefact. In all 7 animals, after verifying that CNAPs could be blocked, blocking was applied continuously for 5 min to check for immediate nerve damage. In all 7 cases CNAPs could be evoked and blocked after this 5 min period. In two animals extended blocking was attempted for 30 minutes before the rest of the experiment, and in both cases CNAPs were able to be evoked and blocked after the 30 minutes of blocking. However, when continuous blocking was attempted for the entire two-hour long experiment during seizure, there was limited success. In one instance, the entire experiment was completed—verified blocking at the beginning, injected kainic acid, applied blocking for two hours, and then verified blocking a second time before euthanasia. This animal did not have acid reflux, displayed normal signs of seizure, and its stomach had a large amount of liquid (1% of total body mass). For a variety of reasons not reported here, the other 6/7 cases were unsuccessful. This technique may be more successful in a chronic model with acute seizure activity, as blocking could be introduced only for a short time, without the confounding effects seen during a two-hour block.

Treatment

Groups 1-3: Gastric Severing:

Severing the gastric nerve significantly reduced acid reflux, sudden death, and the amount of liquid in the stomach. This was the most effective technique, as it had the best survival. These results help address some limitations of the model. One limitation of the acute i.p. KA model is that the drug is administered systemically, so it is possible that some of the response that was seen is not the direct result of seizure activity. The fact that severing this specific nerve reduced acid reflux, sudden death, and the volume of liquid in the stomach suggests that signaling along this nerve is vital to the acid reflux/sudden death mechanism in this model. Gastric vagotomy may have some clinical translation capability. Gastric vagotomies are already commonly performed in patients with GI disorders, such as ulcers or frequent acid reflux. While the procedure does have some side effects, it may be worthwhile for some epilepsy patients. However, side effects for an epilepsy-relevant gastric vagotomy could be more severe. Patients with drug resistant epilepsy and frequent GTCS have a 35% lifetime risk of SUDEP, so a gastric vagotomy may be a reasonable preventative step, even considering side effects.

Groups 4 & 5: Fasting:

Fasting animals significantly reduced acid reflux and sudden death. These animals appeared to be more sensitive to KA than other animals, as they displayed a seizure response typically associated with higher doses of KA. It was hypothesized that fasting the animals may affect the KA dosing. Research in mice has demonstrated that fasting results in a decrease in body mass, but no decrease in brain volume. Therefore, our weight dependent dose of KA may result in a higher amount of KA in the brain, compared to a non-fasted animal of similar weight. The exact pharmacokinetics of how KA accumulates in the brain, and how fasting affects accumulation are not known. However, it was observed that fasted animals that received an 80% dose of KA exhibited seizure responses that were more similar to the nonfasted animals in respiration, ECoG, and physical observations than the fasted animals that received the 100% dose. Fasting is the most accessible potential translational treatment. If effective, fasting before bed, which is when most SUDEP cases occur, could help reduce mortality.

The vagus nerve is significantly involved in several mechanisms of stomach acid production. The vagus nerve mediates acid production triggered by the sight and smell of food, as well as production triggered by distension of the stomach wall. It was hypothesized that seizure activity may initiate stomach acid production, which is exacerbated by aerophagia, and result in a positive feedback loop in which stomach distension triggers even more acid production. Acid production pathways have negative feedback loops to prevent excess stomach acid production, and the large increase in liquid volume that was observed suggests that these pathways may malfunction during these experiments as well. It was hypothesized that stomach pressure may increase until the esophageal sphincters fail, allowing acid movement into the esophagus. The esophageal sphincters are also innervated by the vagus nerve, and may malfunction during seizure, contributing to the mechanism. It is possible that fasting may reduce the starting volume in the stomach such that this process is sufficiently delayed so that it does not occur during our experimental window, or, in a clinical setting, before a patient recovers from a seizure. It is likely that fasting only delays the mechanism that were observed, but a delay may still have clinical relevance.

Group 6: Laryngeal Stimulation:

These experiments demonstrated that it is possible to open the larynx during acid-induced laryngospasm. Acid inspiration, even if it causes lasting damage, is certainly preferable to sudden death. Many patients with drug resistant epilepsy have vagal nerve stimulation (VNS) devices. These devices deliver frequent, low amplitude stimulation to the vagus nerve, which can reduce seizure frequency and severity for some patients. A treatment mechanism could take advantage of this existing technology and could reach many patients. Stimulation was applied to the laryngeal nerve directly, but these nerves are vagal tracts, which could be stimulated by stimulating the cervical vagus at the site of a VNS device. Therefore, this therapy, if effective, could reach many patients with minimal additional costs.

Further Implications:

Laryngeal stimulation may have clinical relevance outside of epilepsy. Some children with chronic aerodigestive disorders will experience laryngospasm as an acute crisis event. In these cases, laryngospasm is often caused not by a low pH, but by mechanical stimulation of the larynx due to eating or drinking, often in children born premature with aerodigestive orders such as laryngomalacia, spasmodic croup, or subglottic stenosis. In these cases, laryngeal stimulation could open the larynx without fear of acid causing permanent damage to the lungs.

Difference in Laryngospasm Presentation:

A noticeable difference in laryngospasm response was observed between seizing and non-seizing animals. Seizing animals that experienced obstructive apnea never recovered, and the time from obstructive apnea onset to terminal apnea was within 5 minutes for all cases. Conversely, the non-seizing animal was able to survive 5 obstructive apneas over more than one hour (with time for recovery in between). These data suggest that seizing animals may die "too quickly" from obstructive apnea, which may imply an additional mechanism that follows laryngospasm.

The laryngeal chemoreflex (LCR) is present in many young mammals, including humans, and causes central apnea, bradycardia, laryngeal closure, and hypotension in response to laryngeal stimulation. In many cases the response is mild and recoverable, but, in some cases, it is severe and fatal. The reflex may be caused by water, acid, or mechanical stimulation, including laryngospasm. The LCR is only evident early in life, often disappearing within the first year for humans, when it is replaced by diving and choking reflexes and fear response. The LCR may be relevant to sudden infant death syndrome. The apnea seen in the LCR may be related to medullary respiratory centers in the brainstem. The LCR response may be more severe if animals are already hypoxic. It is therefore possible, if this reflex is still present in adult animals, that an obstructive apnea could trigger a subsequent central apnea. This central apnea may be severe enough to be fatal, and the severity of the reflex may be exacerbated by hypoxia from previous ictal apneas. This reflex may depress respiratory signals in the brainstem, which may contribute to brainstem depolarization, which has been observed by others during seizure. The LCR may explain why seizing animals appear to be more susceptible to death from obstructive apnea and show respiratory effort for a shorter duration than non-seizing animals. There may be a link between the LCR, laryngospasm, and brainstem depression, which has by implicated by others in SUDEP.

Group 7: Gastric Blocking:

Electrical blocking of this nerve is possible, reversible, and safe, if used for less than 5 minutes. In the experimental setup, animals experience seizure activity for several hours, but clinical seizures typically only last a few minutes. Electrical blocking could be effective in such a setting where seizures are short enough that the applied block can be short. Such a therapy could have clinical relevance as it may be implemented on existing VNS devices and the blocking stimulation may not cause significant side effects during its short application.

Proposed Mechanism:

Seizure activity may send malfunctioning signals via the gastric branch of the vagus nerve to the stomach. These signals, through some combination of gastric branch signaling and possibly other acid production pathways, result in an increase in fluid volume in the stomach. This increase in fluid volume, possibly aggravated by aerophagia, possibly aggravated by seizure activity weakening the esophageal sphincters, results in acid reflux into the esophagus. Acid moves up to the larynx, where it ultimately triggers laryngospasm and obstructive apnea. Obstructive apnea may itself be sufficient for death, or obstructive apnea may activate pathways of the LCR, which act to depress the brainstem.

Hypoxia from obstructive apnea may end the seizure, and hypoxia and postictal depression may also contribute to brainstem depression. The depressed brainstem may contribute to brainstem depolarization, and ultimately trigger terminal central apnea and asystole. There was no data to suggest that brainstem depolarization is dependent upon laryngospasm, but rather that laryngospasm may be a contributing factor in a more universal mechanism.

Therapy Solutions

Figure 8:
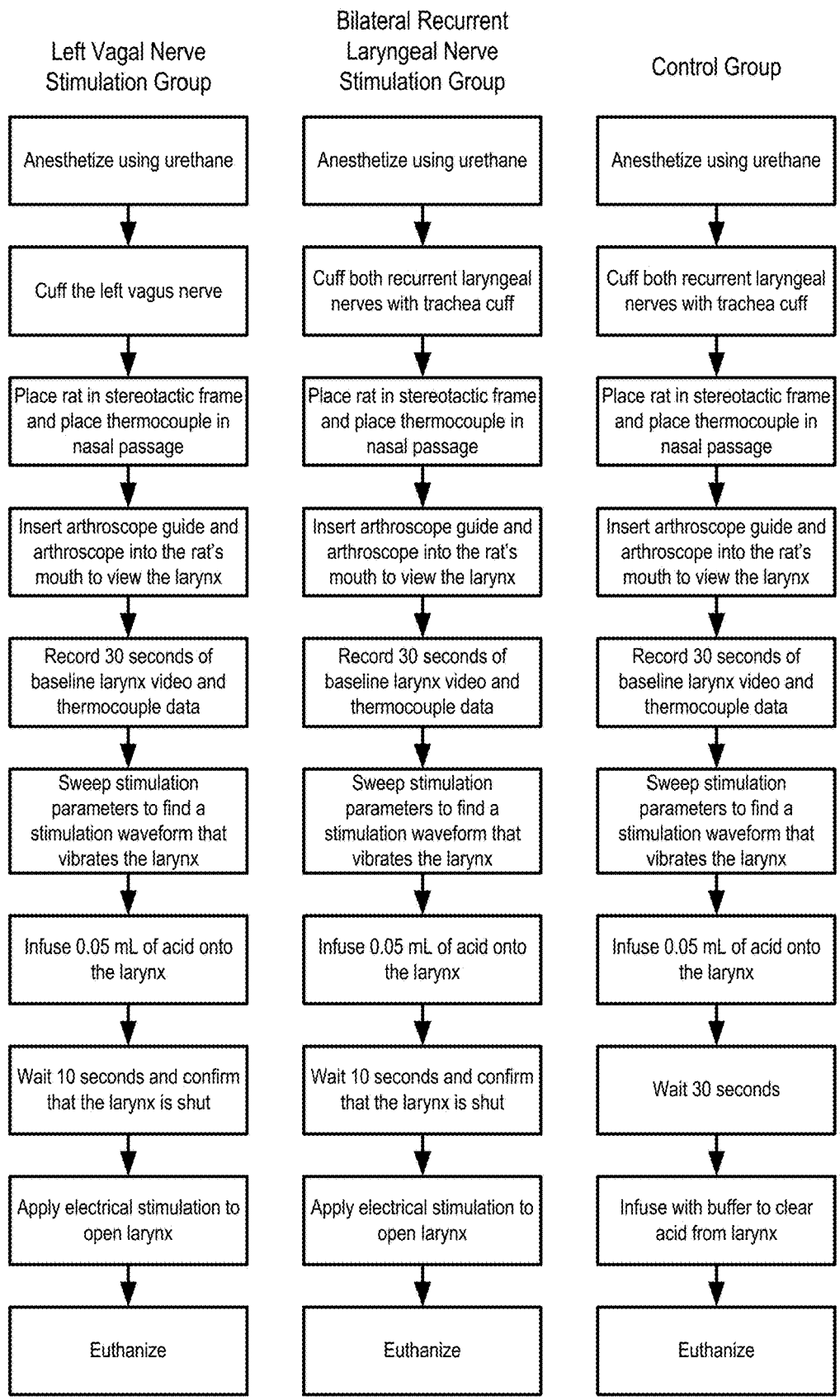
FIG. 8 is a series of flowcharts showing processes for assessing the impact of various stimulation on rats, in accordance with some embodiments provided herein.

In light of the experimental findings set forth above, various therapy solutions can be used to prevent acid reflux induced laryngospasm and any associated pathology resulting therefrom, including (but not limited to) sudden death in epilepsy (SUDEP) and sudden infant death syndrome (SIDS). These solutions can include the use of an implantable stimulator to perform laryngeal nerve stimulation or vagal nerve stimulation. FIG. 8 illustrates the protocols employed for assessing the impact of both types of stimulation on rats.

Laryngeal nerve stimulation (such as, recurrent laryngeal nerve (RLN) stimulation) serves to open up the larynx to overcome the closure that otherwise occurs during laryngospasm, which advantageously returns airflow to the subject to prevent sudden death. Vagal nerve stimulation (such as, left vagal nerve stimulation) serves this same larynx-opening function, but also prevents the overproduction of stomach acid that would otherwise occur during laryngospasm. In so doing, vagal nerve stimulation offers two separate manners of preventing sudden death due to acid reflux induced laryngospasm.

The stimulation techniques disclosed herein (vagal nerve or RLN) may be accomplished via the implantable electroceutical of the type shown and described in FIGS. 16-20 of the 079 PCT and FIG. 1 of the present disclosure. It is also contemplated to add this functionality to existing vagal nerve stimulators, which would have the added benefit of not requiring the implantation of a separate stimulator. Regardless of the type of implantable stimulator, the proposed solutions for preventing acid reflux induced laryngospasm include, but are not limited to, those shown in FIGS. 9-12.

For example, the implantable stimulator, or a separate monitoring system, can detect a reflux, a respiratory change, and/or a laryngospasm. Detection can include detecting pH levels from a pH sensor in the esophagus, electrical activity of the diaphragm muscles, electrical activity of the intercostal muscles, and/or movement of air in and out of the lungs. In some cases, movement of air in and out of the lungs can be detected using a thermistor (e.g., in a nostril or mouth).

Such detection can be provided by an external device, or an implantable device. In some cases, once a reflux, a respiratory change, and/or a laryngospasm is detected, an alert can be sent to a caregiver. The caregiver can then put the patient in an up right position (e.g., sitting), or apply an external trigger to an implantable device (e.g., a magnetic swipe).

Optionally, such detection can also include detecting a seizure. For example, a seizure can be detected using EEG, ECoG, ECG, and/or an accelerometer. Once a seizure is detected, a nerve can be stimulated to electrically block the nerve, preventing the stomach from filling with acid and refluxing into the larynx. In some cases, the nerve can be a vagus nerve and/or a gastric nerve.

In some cases, once a reflux, a respiratory change, and/or a laryngospasm is detected, electrical stimulation can be provided to open the larynx. For example, electrical stimulation can be provided to the laryngeal nerve. The electrical stimulation can be provided via an implanted device or an external device. For example, the external device can be a wearable, or a device that can be placed on or around the neck by a caregiver. While acid may enter the vocal cords or lungs while the larynx is held open, sudden death may be prevented.

FIG. 9 illustrates a stimulation system 900 for vagal nerve stimulation (VNS), gastric nerve stimulation (GNS), or laryngeal nerve stimulation (LNS) 902 to stop laryngospasm, which is triggered manually 904 via any number of external manners. By way of example only, one such manner of manual triggering could be a magnet swipe initiated by the patient, care-giver, or first-responder when respiratory distress is observed. This stimulation system is simple and can be implemented on current VNS systems with minimal changes (e.g., firmware updates).

FIG. 10 illustrates a stimulation system 910 for vagal nerve stimulation (VNS), gastric nerve stimulation (GNS), or laryngeal nerve stimulation (LNS) 912 to stop laryngospasm, which is triggered whenever a seizure is detected by a seizure detection algorithm 914. A seizure may be detected via any number of suitable technologies, such as (by way of example only) analyzing recorded physiological signals and/or motion sensors 916 (e.g., EEG, ECoG, ECG, and/or accelerometer). In this manner, the stimulation system of FIG. 10 will be able to stop laryngospasms automatically without user input. It may be beneficial to develop techniques for increasing the specificity for laryngospasm such that stimulation won't occur for all seizures, but rather only those involving laryngospasm, which may require input signals beyond those currently measured by existing VNS devices.

FIG. 11 illustrates a stimulation system 920 for vagal nerve stimulation (VNS), gastric nerve stimulation (GNS) or laryngeal nerve stimulation (LNS) 922 to stop laryngospasm, triggered whenever laryngospasm is detected via laryngospasm detection algorithm 924. Laryngospasm may be detected via any number of suitable technologies, such as (by way of example only) analyzing recorded EMG signals from the diaphragm 926 and the larynx 928. In this manner, the stimulation system of FIG. 11 can stop laryngospasms automatically without user input and, moreover, has high specificity to laryngospasm such that stimulation will only occur when laryngospasm is detected. To do so, the stimulation system will require input signals not currently measured by existing VNS devices.

FIG. 12 illustrates a stimulation system 930 for vagal nerve stimulation (VNS), gastric nerve stimulation (GNS), or laryngeal nerve stimulation (LNS) 932 to stop laryngospasm, which is triggered whenever peripheral capillary oxygen saturation ($SpO_2$) levels drop below a critical level as detected by low $SpO_2$ detector 934. The monitoring of $SpO_2$ levels may be accomplished via any number of suitable technologies, such as (by way of example only) pulse oximetry sensors 936 capable of being worn or otherwise on the skin of the patient (vs. implanted). In this manner, the stimulation system 930 of FIG. 12 can stop laryngospasms automatically without user input and, moreover, can do so without the need for an implanted sensor to trigger stimulation. By allowing for a "wearable" $SPO_2$ sensor, the solution of FIG. 12 may be particularly advantageous for preventing SIDS, in that the $SpO_2$ levels may be monitored non-invasively (e.g. via a cuff or collar worn by the infant). If $SpO_2$ levels drop below a critical level, an alarm may sound for the parents to come to the aid of the infant and/or an exteriorly worn VNS stimulator may be activated to overcome the laryngospasm and open the larynx for restored breathing.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A method of preventing sudden death, the method comprising:
   detecting, based on first sensor data collected by a first sensor, seizure activity in a subject;
   identifying, based on second sensor data collected by a second sensor, presence of acid in an esophagus of the subject, wherein the presence of acid is identified during the seizure activity;
   determining that the subject is experiencing acid-induced laryngospasm based at least on the seizure activity and the presence of acid in the esophagus of the subject during the seizure activity; and
   transmitting an electrical stimulation signal to a nerve in response to determination that the subject is experiencing acid-induced laryngospasm.

2. The method of claim 1, wherein the second sensor comprises a pH sensor.

3. The method of claim 1, wherein:
   the first sensor comprises an EMG sensor; and
   determining that the subject is experiencing acid-induced laryngospasm comprises detecting a change in electrical activity of a diaphragm or a larynx via the EMG sensor.

4. The method of claim 1, wherein:
   the first sensor comprises an SpO$_2$ sensor; and
   determining that the subject is experiencing acid-induced laryngospasm comprises detecting a change in oxygen saturation via the SpO$_2$ sensor.

5. The method of claim 1, wherein the electrical stimulation is configured to cause the acid-induced laryngospasm to cease.

6. The method of claim 1, wherein the nerve is a vagus nerve or a gastric nerve.

7. The method of claim 1, wherein the electrical stimulation is triggered by an external input to a wearable device.

8. The method of claim 7, wherein the external input is a magnet swipe.

9. The method of claim 1, wherein the electrical stimulation is configured to prevent at least one of sudden unexplained death from epilepsy (SUDEP) or sudden infant death syndrome (SIDS).

10. The method of claim 1, wherein the acid-induced laryngospasm is detected via a wearable device worn on a neck or an arm of a user.

11. The method of claim 1, wherein determining that the subject is experiencing acid-induced laryngospasm comprises detecting, by a third sensor, a change in heart rate, wherein the third sensor comprises an ECG sensor placed on a neck of a user.

12. The method of claim 1, wherein determining that the subject is experiencing acid-induced laryngospasm comprises:
   measuring changes in movement of air through lungs via a thermistor;
   detecting a cessation of respiration based on the measured changes in the movement of air through the lungs; and
   determining that the subject is experiencing acid-induced laryngospasm based on the cessation of respiration.

13. The method of claim 12, wherein detecting the cessation of respiration comprises detecting a change in electrical activity of a diaphragm or a larynx via an EMG.

14. The method of claim 1, wherein determining that the subject is experiencing acid-induced laryngospasm comprises:
   comparing the one or more data signals to a threshold; and
   determining a deviation from a baseline condition based on comparing the one or more data signals to the threshold; and
   detecting a physiological dysfunction based on determining the deviation from the baseline condition.

15. The method of claim 1, wherein:
   the first sensor comprises an ECG sensor; and
   detecting the seizure activity in the subject comprises detecting the seizure activity via the ECG sensor.

16. The method of claim 1, wherein the first sensor comprises an accelerometer.

17. The method of claim 1, wherein:
   the first sensor comprises an ECG sensor; and
   determining that the subject is experiencing acid-induced laryngospasm comprises:
   determining heart rate variability or a change in heart rate via the ECG sensor; and
   detecting the seizure activity in the subject based on the determining the heart rate variability or the change in heart rate.

18. The method of claim 1, wherein detecting the seizure activity in the subject comprises:
   determining a change in respiration; and
   detecting the seizure activity in the subject based on determining the change in respiration.

* * * * *